US006037325A

United States Patent [19]
Gyorkos et al.

[11] Patent Number: 6,037,325
[45] Date of Patent: *Mar. 14, 2000

[54] SUBSTITUTED HETEROCYCLIC COMPOUNDS USEFUL AS INHIBITORS OF (SERINE PROTEASES) HUMAN NEUTROPHIL ELASTASE

[75] Inventors: Albert Gyorkos, Westminster; Lyle W. Spruce, Arvada, both of Colo.

[73] Assignee: Cortech, Inc., Bedminster, N.J.

[*] Notice: This patent is subject to a terminal disclaimer.

[21] Appl. No.: 09/069,823

[22] Filed: Apr. 30, 1998

Related U.S. Application Data

[63] Continuation of application No. 08/698,575, Aug. 15, 1996, Pat. No. 5,874,585, which is a continuation of application No. 08/345,820, Nov. 21, 1994, Pat. No. 5,618,792.

[51] Int. Cl.$^7$ .......................... A61K 38/06; C07K 5/087; C07K 5/097
[52] U.S. Cl. .............................. 514/18; 530/331; 530/332
[58] Field of Search ............................... 514/18, 19, 361, 514/362, 363, 364, 383; 530/330, 331, 332; 548/128, 131, 136, 143, 266.8

[56] References Cited

U.S. PATENT DOCUMENTS

| | | | |
|---|---|---|---|
| 4,338,453 | 7/1982 | Gall | 548/263 |
| 5,055,450 | 10/1991 | Edwards et al. | 514/19 |
| 5,164,371 | 11/1992 | Edwards et al. | 514/18 |
| 5,618,792 | 4/1997 | Gyorkos et al. | 514/18 |
| 5,801,148 | 9/1998 | Gyorkos et al. | 514/18 |
| 5,807,829 | 9/1998 | Gyorkos et al. | 514/18 |
| 5,861,380 | 1/1999 | Gyorkos et al. | 514/19 |
| 5,874,585 | 2/1999 | Gyorkos et al. | 548/128 |

FOREIGN PATENT DOCUMENTS

| | | | |
|---|---|---|---|
| 0 291 234 | 11/1988 | European Pat. Off. | C07K 5/06 |
| 376 012 | 7/1990 | European Pat. Off. | |
| 0 480 044 | 4/1992 | European Pat. Off. | C07D 413/12 |
| 0 528 633 A1 | 2/1993 | European Pat. Off. | C07D 239/46 |
| 0 529 568 A1 | 3/1993 | European Pat. Off. | C07D 5/08 |
| 2 694 295 | 2/1994 | France | C07K 5/12 |
| 2224338 | 12/1972 | Germany | C07D 85/52 |
| 1397073 | 6/1975 | United Kingdom | C07D 271/06 |
| WO 93/21212 | 10/1993 | WIPO | C07K 5/06 |
| WO 96/16080 | 5/1996 | WIPO | C07K 5/062 |

OTHER PUBLICATIONS

Edwards, P. D. et al., "Peptidyl Alpha–Ketoheterocyclic inhibitor of Human Neutrophil Elastase. 3. In Vitro and in Vivo Potency of a Series of Peptidyl Alpha–Ketobenzoxazoles," J. Med. Chem. 38: 3972–3982 (1995).
Edwards, P. D. et al., "Nonpeptic Inhibitors of Human Neotrophil Elastase. 7. Design, Synthesis, and in Vitro Activity of a Series of Pyridopyrimidine Trifluoromethyl Ketones," J. Med. Chem. 39: 1112–1124 (1996).
Edwards, P. D. et al., "Petidyl Alpha–Ketoheterocyclic Inhibitors of Human Neutrophil Elastase. 2. Effect of Varying the Heterocyclic Ring on in Vitro Potency," J. Med Chem. 38: 76–85 (1995).

Veale, C. A. et al., "Non–peptidic Inhibitors of Human Leukocyte Elastase. 4. Design, Synthesis, and in Vitro and In Vivo Activity of a Series of Beta–Carbolinone–Containing Trifluoromethyl Ketones," J. Med. Chem. 38: 86–97 (1995).
Veale, C. A. et al., "Nonpeptidic Inhibitors of Human Leukocyte Elastase. 5. Design, Synthesis, and X–ray Crystallography ofa Series of Orally Active 5–Aminopyrimidin–6–one–Containing Trifluoromethyl Ketones," J. Med. Chem. 38: 98–108 (1995).
Goddard, C. J., "Antiinflammatory 1–Phenylpyrazole–4–Heteroarylalkanoic Acids," J. Heterocyclic Chem. 28: 1607–1612 (1991).
LaMattina, J. L. et al., "Utility of 24 p–Nitrophenyl 3–Bromo–2,2–diethoxypropionate (NPBDP) in Neterocyclic Synthesis," J. Org. Chem. 49: 4800–4805 (1984).
Unangst, P. C. et al., "Novel 1,2,4–Oxadiazoles and 1,2, 4–Thiadiazoles as Dual 5–Lipoxygenase and Cycloioxygenase Inhibitors," J. Med. Chem. 35: 3691–3698 (1992).
Kitatani, K. et al., "A Novel Oxazole Synthesis Utilizing Tungsten(VI) Catalyzed Decomposition of Alpha–Diazo Carbonyl Compounds in Nitriles," Tet. Lett. 16: 1531–1532 (1974).
Wiley, R. H., "Chemistry of the Oxazoles," Chem. Rev. 37: 401–442 (1945).
Davidson, D. et al., "The Action of Ammonia on Bension," J. Org. Chem. 2: 328–334 (1937).
Wiegand, Edwin E. et al., "Polyphosphoric Acid Cyclization of Acetamidoketones to 2,5–Dimethyl–1,3–oxazoles," Synthesis 12: 648–649 (1970).
Wasserman, H.H. et al., "The Oxazole–Triamide Rearrangement. Application To Peptide Synthesis," Tet. Lett. 23(37): 3831–3834 (1982).
Comforth, J. W. et al., "A New Synthesis of Oxazoles and Iminazoles including its Application to the Preparation of Oxazole," J. Chem Soc. 96–102 (1947).
Comforth, J. W. et al., "Synthesis of Oxazoles from Ethyl Acetoacetate. Ring–fission of Some Oxazole–5–carboxylic Acids," J. Chem. Soc. 93–98 (1953).
Bernstein, P. R. et al., "Nonpeptidic Inhibitors of Human Leukocyte Elastase. 3. Design, Synthesis, X–Ray Crystallographic Analysis, and Structure—Activity Relationship for a Series of Orally Active 3–Amino–6–phenylpyridin–2–one Trifluoromethyl Ketones," J. Med. Chem. 37: 3313–3326 (1994).
Brown, F. J. et al., "Design of Orally Active, Non–Peptidic Inhibitors of Human Lekocyte Elastase," J. Med. Chem. 37: 1259–1261 (1994).

(List continued on next page.)

*Primary Examiner*—Jeffrey E. Russel
*Attorney, Agent, or Firm*—Dechert Price & Rhoads

[57] ABSTRACT

The present invention relates to certain substituted oxadiazole, thiadiazole and triazole peptoids which are useful as inhibitors of serine proteases including human neutrophil elastase, equivalently known as human leukocyte elastase.

12 Claims, 4 Drawing Sheets

OTHER PUBLICATIONS

Warner, P. et al., "Non–peptidic Inhibitors of Human Leukocyte Elastase. 1. The Design and Synthesis of Pyridone–Containing Inhibitors," J. Med. Chem. 37: 3090–3099 (1994).

Budavari, Susan (Editor), "The Merck Index," An Encylopedia of Chemicals, Drugs, and Biologicals; Merck & Co., Inc.: 294 (1989).

Damewood, J. R., Jr. et al. "Nonpeptidic Inhibitors of Human Leukocyte Elastase. 2. Design, Synthesis, and in vitro Activity of Series of 3–Amino–6–arylopyridin–2–one Trifluormethyl Ketones," J. Med. Chem. 37: 3303–3312 (1994).

Browne, "Azole Aldehyde Condensations," Aust. J. Chem. 26: 1809–1814 (1973).

Skiles, J.W., et al. "Elastase Inhibitors Containing Conformationally Restricted Lactams as $P_3$–$P_2$ Dipeptide Replacements," Bio. & Med. Chem. Ltrs. 3, 773–778 (1993).

REACTION SCHEME I

REACTION SCHEME II

REACTION SCHEME III

SUBSTITUTED HETEROCYCLIC COMPOUNDS USEFUL AS INHIBITORS OF (SERINE PROTEASES) HUMAN NEUTROPHIL ELASTASE

This is a continuation of application Ser. No. 08/698,575, filed Aug. 15, 1996, now U.S. Pat. No. 5,874,585, which is a continuation of application Ser. No. 08/345,820, filed Nov. 21, 1994, now U.S. Pat. No. 5,618,792.

The present invention relates to certain substituted oxadiazole, thiadiazole and triazole peptoids which are useful as inhibitors of serine proteases including human neutrophil elastase, equivalently known as human leukocyte elastase.

BACKGROUND OF THE INVENTION

Human neutrophil elastase (HNE) is a proteolytic enzyme secreted by polymorphonuclear leukocytes (PMNs) in response to a variety of inflammatory stimuli. This release of HNE and its extracellular proteolytic activity are highly regulated and are normal, beneficial functions of PMNs. The degradative capacity of HNE, under normal circumstances, is modulated by relatively high plasma concentrations of $\alpha_1$-proteinase inhibitor ($\alpha_1$-PI). However, stimulated PMNs produce a burst of active oxygen metabolites, some of which (hypochlorous acid for example) are capable of oxidizing a critical methionine residue in $\alpha_1$-PI. Oxidized $\alpha_1$-PI has been shown to have limited potency as an HNE inhibitor and it has been proposed that alteration of this protease/antiprotease balance permits HNE to perform its degradative functions in localized and controlled environments.

Despite this balance of protease/antiprotease activity, there are several human disease states in which a breakdown of this control mechanism is implicated in the pathogenesis of the condition. Improper modulation of HNE activity has been suggested as a contributing factor in adult respiratory distress syndrome, septic shock and multiple organ failure. A series of studies also have indicated the involvement of PMNs and neutrophil elastase in myocardial ischemia-reperfusion injury. Humans with below-normal levels of $\alpha_1$-PI have an increased probability of developing emphysema. HNE-mediated processes are implicated in other conditions such as arthritis, periodontal disease glomerulonephritis, dermatitis, psoriasis, cystic fibrosis, chronic bronchitis, atherosclerosis, alzheimers disease, organ transplantation, corneal ulcers, and invasion behavior of malignant tumors.

There is a need for effective inhibitors of HNE as therapeutic and as prophylactic agents for the treatment and/or prevention of elastase-mediated problems.

SUMMARY OF THE INVENTION

The principal object of the present invention is to provide certain new compounds which are useful as serine protease inhibitors, including human neutrophil elastase. These compounds are characterized by their relatively low molecular weight, high potency and selectivity with respect to HNE. They can be used effectively to prevent, alleviate or otherwise treat disease states characterized by the degradation of connective tissue by proteases in humans.

The novel compounds of the invention may be structurally illustrated by the following Formula (A):

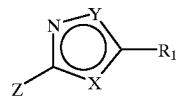

Where Z is a carbonyl containing, preferably an aminocarbonyl-containing group, X and Y are independently O, S or N, provided that at least one of X and Y is N, and $R_1$ is alkyl, haloalkyl, alkenyl, haloalkenyl, alkynyl, phenyl, phenylalkenyl, phenylalkyl or a heteroaryl group. Typically, Z is,

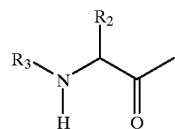

where $R_2$ is a substituted or unsubstituted alkyl, alkoxy, alkylthio, phenyl or cycloalkyl and $R_3$ is a carbonyl-containing moiety; or Z is any other equivalent carbonyl-containing moiety which does not affect the ability of the compound to inhibit serine proteases.

The invention also contemplates intermediates for preparing the compounds of Formula (A), the intermediates being represented by Formula (B) as follows:

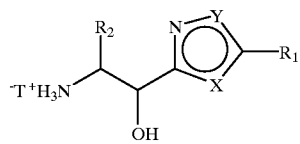

where T is a strong acid that will protonate the free amine and X, Y, $R_1$ and $R_2$ are as defined above.

BRIEF DESCRIPTION OF THE DRAWINGS

FIG. 2 describes the synthesis of 1-[3-[5-substituted]-1, 2,4-oxadiazolyl]-1-acetoxy-2-benzyloxycarbonylamino-3-methyl-butane; and FIG. 3 describes the synthesis of (benzyloxycarbonyl)-L-valyl-N-[1-3-[5-substituted]-1,2,4-oxadiazolyl]carbonyl]-2-(S)-methylpropyl]-L-prolinamide.

DETAILED DESCRIPTION

Figure 1:
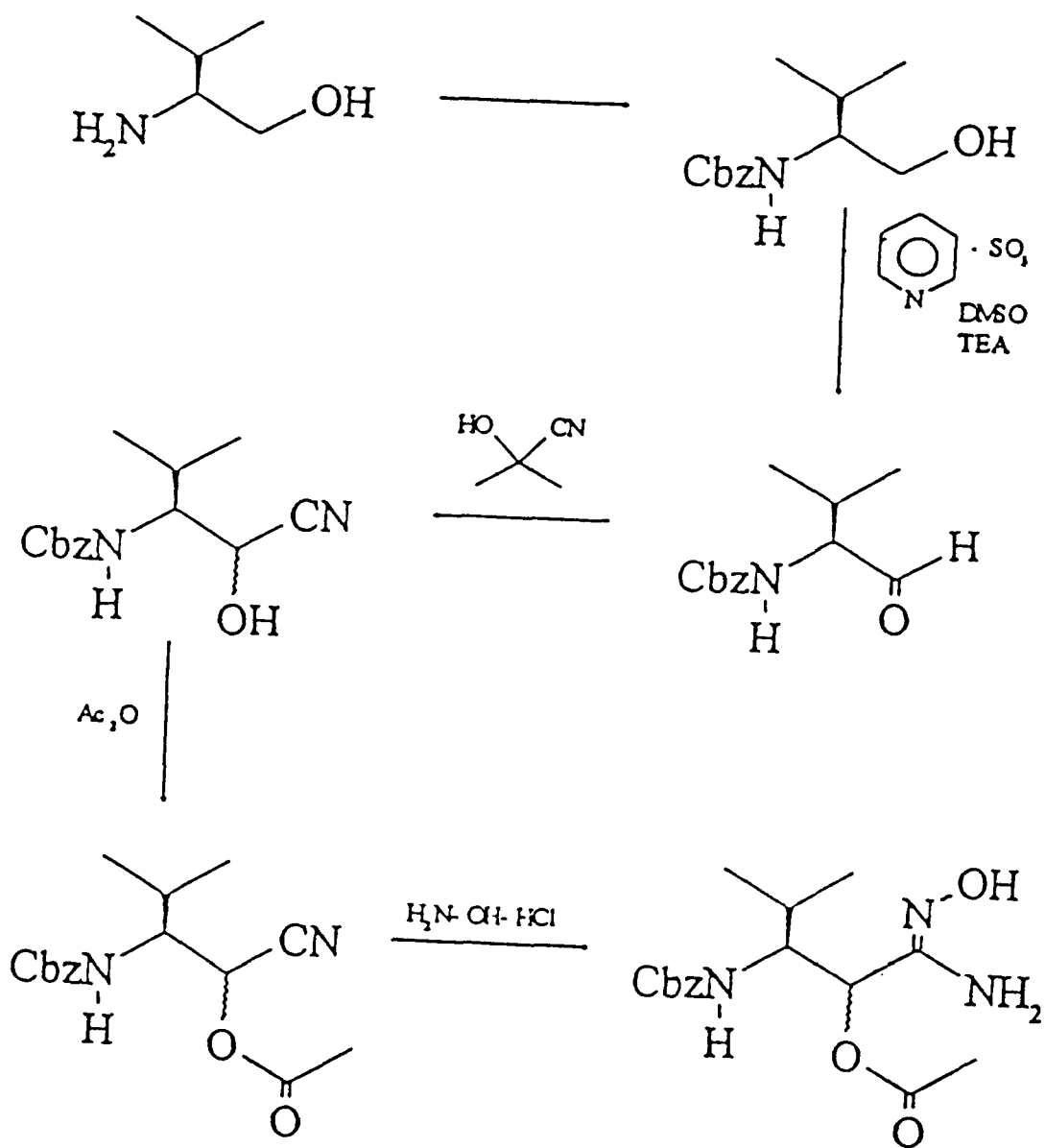
FIGS. 1–3 illustrate the synthesis of compounds according to the invention. In particular, FIG. 1 describes the synthesis of 1-[(N-hydroxy) carboximidamido]-1-acetoxy-2-benzyloxycarbonylamino-3-(S)-methyl-butane.
Figure 2:
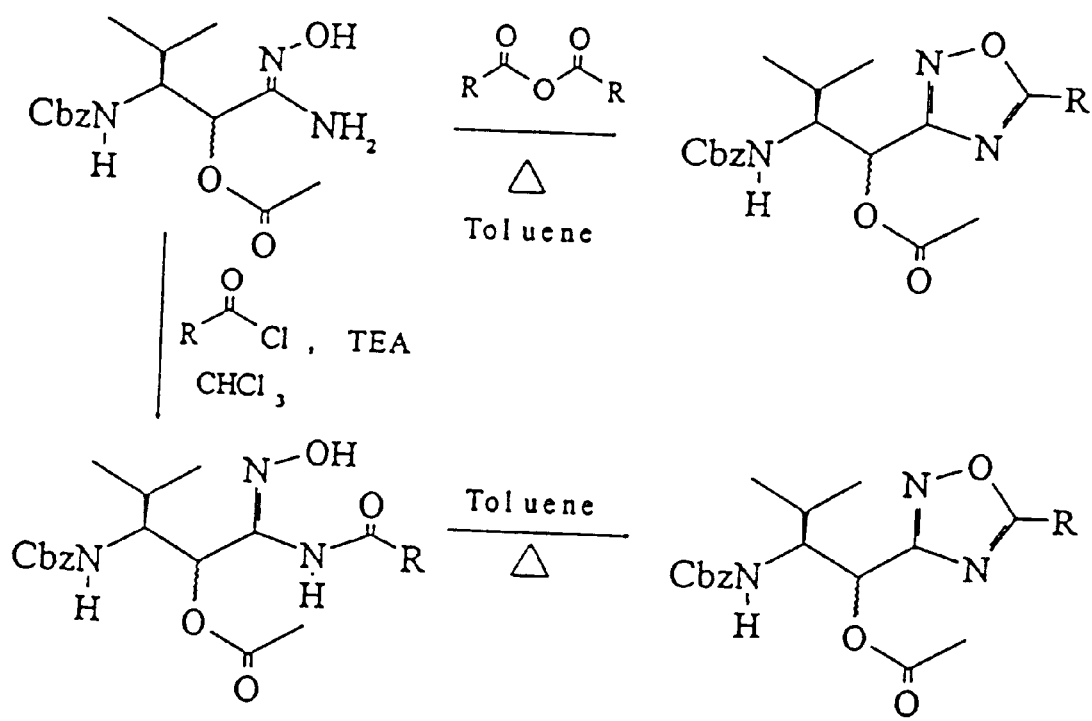
Figure 3:
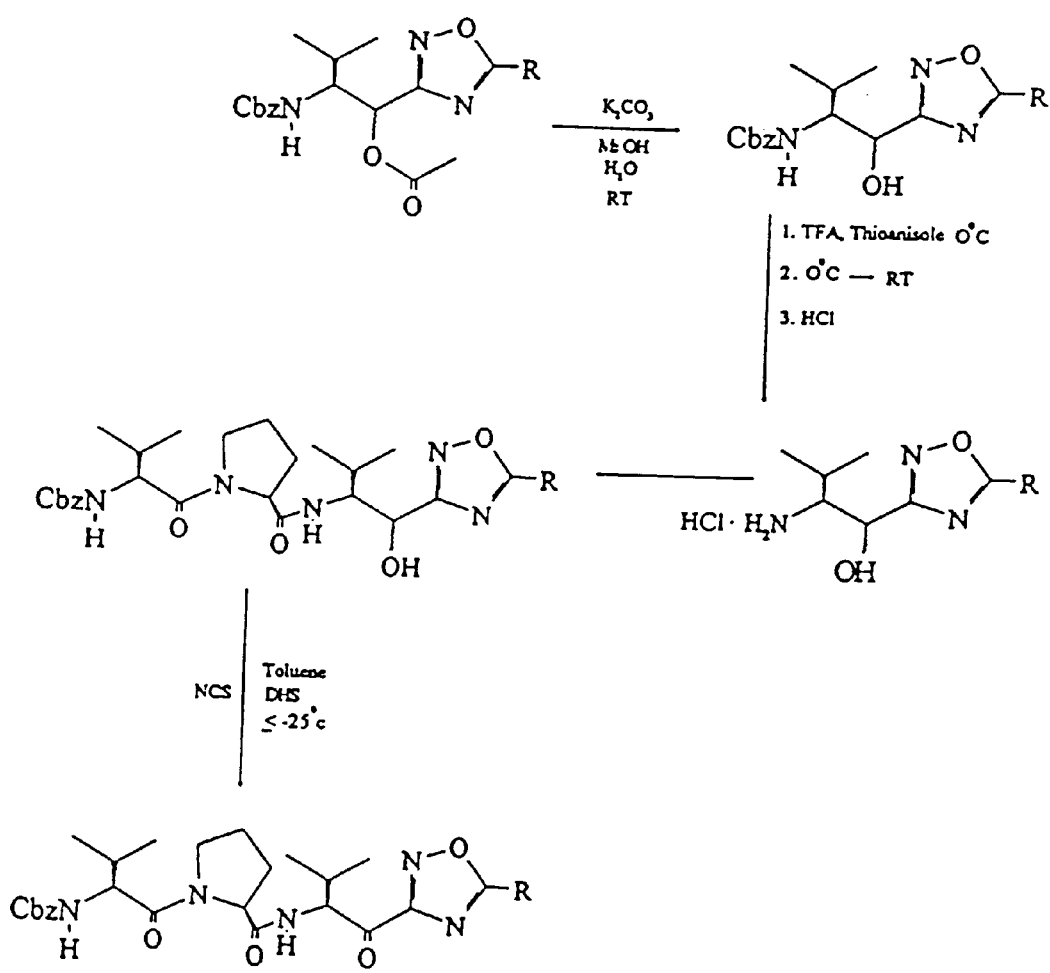

As noted, the invention is directed to substituted heterocyclic compounds which have demonstrated activity against human elastase (HLE), also referred to as human neutrophil elastase (HNE).

The novel compounds of the invention may be structurally illustrated by the following Formula (A):

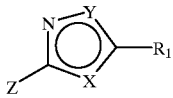

where Z is a carbonyl containing group, preferably an aminocarbonyl-containing, X and Y are independently O, S or N, provided that at least one of X and Y is N, and $R_1$ is alkyl, haloalkyl, alkenyl, haloalkenyl, alkynyl, phenyl, phenylalkenyl, phenyalkyl or a heteroaryl group. Typically, Z is,

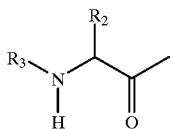

where $R_2$ is a substituted or unsubstituted alkyl, alkoxy, alkylthio, phenyl or cycloalkyl and $R_3$ is a carbonyl-containing moiety; or Z is any other equivalent carbonyl-containing moiety which does not affect the ability of the compound to inhibit serine proteases.

The invention also contemplates intermediates for preparing the compounds of Formula (A), the intermediates being represented by Formula (B) as follows:

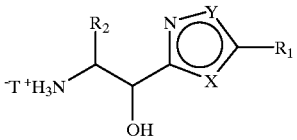

where T is a strong acid that will protonate the free amine and X, Y, $R_1$ and $R_2$ are as defined above.

The compounds of the invention may be further described as pseudopeptides substituted with (1, 2, 4) or (1, 3, 4) thia- or oxa-diazoles or triazoles as illustrated below:

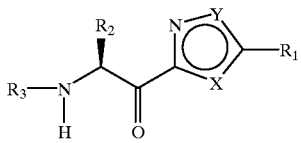

wherein $R_3$ is defined above and further $R_1$ is alkyl, alkenyl, haloalkenyl, alkynyl being linear or branched, a phenyl, phenylalkenyl, or phenylalkyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio, or haloalkylthio groups being linear or branched, a heteroaryl, heteroarylalkyl or heteroarylalkenyl wherein the heteroaryl groups being monocyclic five or six membered containing one or two heteroatoms such as oxygen, sulfur, or nitrogen in any combination and being optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamide, arylcarboxamide, alkylthio, or haloalkylthio groups being linear or branched.

X and Y are independently selected from oxygen or sulfur and nitrogen optionally substituted with alkyl, alkenyl, alkynyl being linear or branched, a phenyl, phenylalkyl, or phenylalkenyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio, or haloalkylthio groups being linear or branched, a heteroaryl, heteroarylalkyl or heteroarylalkenyl wherein the heteroaryl groups being monocyclic five or six membered containing one or two heteroatoms such as oxygen, sulfur, or nitrogen in any combination and being optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamide, arylcarboxamide, alkylthio, or haloalkylthio groups being linear or branched so as to maintain the five membered aromatic heterocycle, provided that at least one of X or Y is nitrogen. It is also preferred that where X or Y is a substituted nitrogen, the other is not a substituted nitrogen.

$R_2$ is a linear or branched alkyl, alkylthio, alkylthioalkyl, alkoxy, cycloalkyl, alkylcycloalkyl, phenyl or phenylalkyl optionally substituted with terminal guanidine, halogen, cyano, nitro, hydroxy, haloalkyl, alkylthio, guanidine, alkyl guanidine, dialkyl guanidine or amidine.

In a particular embodiment of the invention, $R_3$ is the following Formula I;

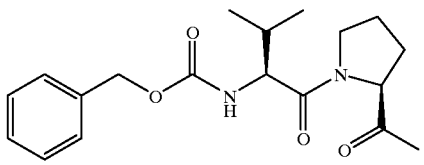

$R_1$ is an optionally substituted phenylalkenyl, phenylalkyl, heteroarylalkyl or heteroarylalkenyl; Y and X are selected from optionally substituted N, S, and O, provided that X or Y is N; and $R_2$ is 2-propyl, benzyl, 3-guanidinyl or 4-amidinylbenzyl.

The preferred $R_2$ substituents include isopropyl, benzyl, 3-guanidinyl and 4-amidinylbenzyl.

According to an additional embodiment of the invention, $R_1$ is an optionally substituted phenylalkyl; Y is O; X is N; and $R_2$ is 2-propyl.

The $R_1$ substituent is preferably chosen from the following: trifluoromethyl, methyl, difluoromethyl, 2,6-difluorobenzyl, benzyl, 2-phenylethyl, 3-methoxybenzyl, 3-phenylpropyl, 3-trifluoromethylbenzyl, 2-methoxybenzyl, 2-trifluoromethylphenylcholoromethyl, 3-thienylmethyl, styryl, 4-trifluoromethylstyryl, 4-methoxystyryl, 4-methoxybenzyl, or phenyl.

As used herein, the term "optionally substituted" means, when substituted, mono to fully substituted.

As used herein, the term "alkyl" means $C_1$–$C_{15}$, however, preferably $C_1$–$C_7$.

As used herein, the term "alkenyl" means $C_1$–$C_{15}$, however, preferably $C_1$–$C_7$.

As used herein, the term "alkynyl" means $C_1$–$C_{15}$, however, preferably $C_1$–$C_7$.

As used herein, the term "aryl" is synonymous with "phenyl" and unless otherwise stated is optionally substituted.

The oxadiazoles of the present invention have been found to be potent inhibitors of the serine protease human neutrophil elastase (HNE). These compounds can be regarded as reversible inhibitors that presumably form a transition state intermediate with the active site serine residue. These oxadiazoles can be characterized by their low molecular weights, high selectivity with respect to HNE and stability regarding physiological conditions. Therefore, these compounds can be implemented to prevent, alleviate and/or otherwise treat diseases which are mediated by the degradative effects associated with the presence of HNE. Their usage is of particular importance as they relate to various human treatment in vivo but may also be used as a diagnostic tool in vitro.

As described above, $R_3$ may also be a moiety which contributes to the oral activity of the compound. Techniques for conferring oral activity onto a compound are well known in the art. By way of example only, $R_3$ may be chosen from Formulas II–VI, described below:

Formula II

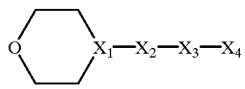

where $X_1$ is N or CH; $X_2$ is a group of the formula:

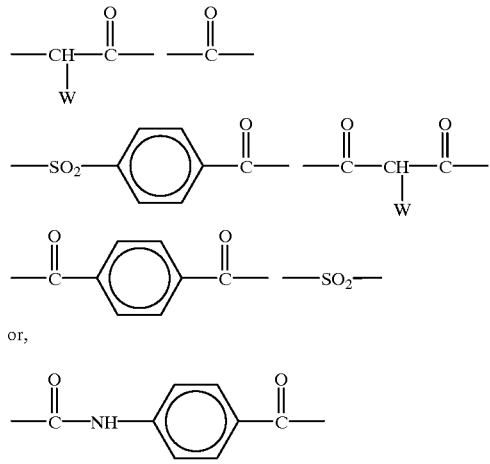

or, where W is H, or alkyl straight chained or branched; $X_3$ is Ala, bAla, Leu, Ile, Val, Nva, bVal, Met, or Nle or an N-methyl derivative or a bond; and $X_4$ is an amino acid consisting of proline, isoleucine, leucine, cyclohexylalanine, cysteine optionally substituted at the sulfur with alkyl, alkenyl, being linear or branched or phenyl optionally substituted with halogen, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio, haloalkylthio groups being linear or branched, a phenylalanine, indoline-2-carboxylic acid, tetrahydroisoquinoline-2-carboxylic acid optionally substituted with alkyl, alkenyl, haloalkenyl, alkynyl being linear or branched, halogen, cyano, nitro, haloalkyl, amino, aminoalkyl, dialkylamino, alkoxyl, haloalkoxy, carbonyl, carboalkoxy, alkylcarboxamide, arylcarboxamide, alkylthio, or haloalkylthio group being linear or branched, tryptophan, valine, norvaline, norleucine, octahydroindole-2-carboxylic acid, lysine optionally substituted with alkylcarboxy or arylcarboxy, glycine optionally substituted at the nitrogen with alkyl, cycloalkyl, phenyl, bicycloalkyl, heteroaryl, alkenyl, alkynyl, cycloalkyl alkyl, bicycloalkyl alkyl, alkoxyalkyl, alkylthioalkyl, alkylaminoalkyl, fused aryl-cycloalkyl alkyl, fused heteroarylcycloalkyl alkyl, dialkylaminoalkyl, carboxyalkyl or alkoxycarbonyl alkyl.

$R_3$ may also be:

Formula III

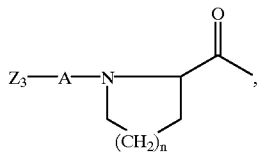

Formula IV

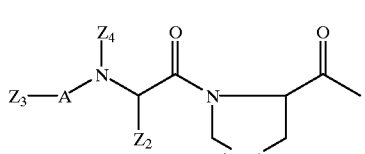

or

Formula V

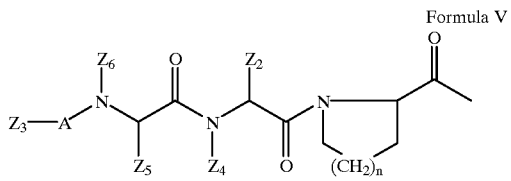

wherein $Z_2$ and $Z_5$ are optionally substituted alkyl, aryl, or arylalkyl; $Z_3$ is optionally substituted alkyl, cycloalkyl, alkenyl, aryl, arylalkyl, an aliphatic heterocycle, or aromatic heterocycle; $Z_4$ and $Z_6$ are hydrogen or methyl; A is selected from the group consisting of

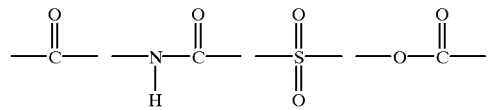

and n is 0, 1 or 2;

In addition, $R_3$ may be represented by the following:

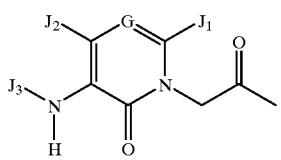

where G is nitrogen or carbon; $J_1$ and $J_2$ are independently substituted with hydrogen, alkyl, cycloalkyl, aryl, heteroaryl, alkylaryl or alkylheterolaryl and $J_3$ is selected from hydrogen, acyl either alkyl, aryl or alkylaryl, alkyl-SO$_2$—, aryl-SO$_2$—, alkylaryl-SO$_2$—, heterocycle-SO$_2$—, alkyl-NH—SO$_2$—, aryl-NH—SO$_2$—, alkylaryl-NH—SO$_2$—, or heterocycle-NH—SO$_2$—. When G is carbon then this carbon may be substituted with hydrogen, alkyl, cycloalkyl, aryl, heteroaryl, alkylaryl or alkylaryl.

Another important embodiment of the invention is the provision of novel intermediates of the Formula (B) as follows:

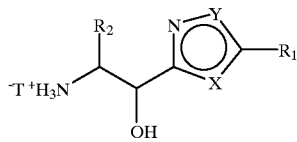

where T is a strong acid that will protonate the free amine and X, Y, $R_1$ and $R_2$ are as defined above.

Methods for synthesizing the above mentioned $R_3$ constituents are described in EPA 0 529 568 A1 (Formula II); U.S. Pat. No. 5,055,450 (Formula III–V); EPA 0 528 633; Warner et at., *J. Med. Chem.*, 37:3090–3099 (1994); Damewood et al., *J. Med. Chem.*, 37:3303–3312 (1994); Bernstein et al., *J. Med. Chem.*, 37:3313–3326 (1994)(Formula VI).

Figure 4:
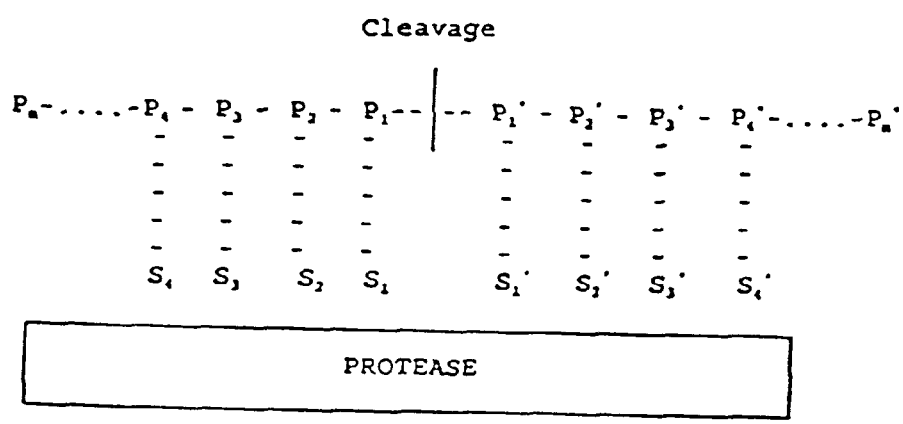
FIG. 4 illustrates substrate and enzyme subsite binding.

The compounds of the present invention are not limited to use for inhibition of human elastase. Elastase is a member of the class of enzymes known as serine proteases. This class also includes, for example, the enzymes chymotrypsin, cathepsin G, trypsin and thrombin. These proteases have in common a catalytic triad consisting of Serine-195, Histidine-57 and Aspartic acid-102 (chymotrypsin numbering system). The precise hydrogen bond network that exists between these amino acid residues allows the Serine-195 hydroxyl to form a tetrahedral intermediate with the carbonyl of an amide substrate. The decomposition of this intermediate results in the release of a free amine and the acylated enzyme. In a subsequent step, this newly formed ester is hydrolyzed to give the native enzyme and the carboxylic acid. It is this carboxyl component that helps characterize the specificity for the enzyme. In the example in which the carboxyl component is a peptide, the alpha-substituent of the amino acid is predominately responsible for the specificity toward the enzyme. Utilizing the well accepted subsite nomenclature by Schechter and Berger (*Biochem. Biophys. Res. Commun.* 27:157(1967) and *Biochem. Biophys. Res. Commun.* 32:898 (1968), the amino acid residues in the substrate that undergo the cleavage are defined as $P_1 \ldots P_n$ toward the N-terminus and $P_1' \ldots P_n'$ toward the C-terminus. Therefore, the scissile bond is between the $P_1$ and the $P_1'$ residue of the peptide subunits. A similar nomenclature is utilized for the amino acid residues of the enzyme that make up the binding pockets accommodating the subunits of the substrate. The difference is that the binding pocket for the enzyme is designated by $S_1 \ldots S_n$ instead of $P_1 \ldots P_n$ as for the substrate (FIG. 4).

The characteristics for the $P_1$ residue defining serine proteinase specificity is well established (see Table 1). The proteinases may be segregated into three subclasses: elastases, chymases and tryptases based on these differences in the $P_1$ residues. The elastases prefer small aliphatic moieties such as valine whereas the chymases and tryptases prefer large aromatic hydrophobic and positively charged residues respectively.

One additional proteinase that does not fall into one of these categories is prolyl endopeptidase. The $P_1$ residue defining the specificity is a proline. This enzyme has been implicated in the progression of memory loss in Alzheimer's patients. Inhibitors consisting of α-keto heterocycles have recently been shown to inhibit prolyl endopeptidase; Tsutsumi et. al., *J. Med. Chem.* 37: 3492:3502 (1994). By way of extension, α-keto heterocycles as defined by Formula I allow for an increased binding in P' region of the enzyme.

TABLE 1

$P_1$ characteristics for Proteinase Specificity

| PROTEINASE | REPRESENTATIVE | $P_1$ |
|---|---|---|
| Elastases | Human Neutrophil Elastase | small aliphatic residues |
| Chymases | alpha-Chymotrypsin, Cathepsin G | aromatic or large hydrophobic residues |
| Tryptases | Thrombin, Tryptin, Urokinase, Plasma Killikrein, Plasminogen Activator, Plasmin | positively charged residues |
| Other | Prolyl, Endopeptidase | proline |

Since the $P_1$ residue predominately defines the specificity of the substrate, the present invention relates to $P_1-P_n'$ modifications, specifically, certain alpha-substituted keto-heterocycles composed of 1,3,4 oxadiazoles, 1,2,4-oxadiazoles, 1,3,4-thiadiazoles, 1,2,4-thiadiazoles, 1-substituted, and 4-substituted 1,2,4-triazoles. By altering the alpha-substituent and the substituent on the heterocycle, the specificity of these compounds can be directed toward the desired proteinase (e.g., small aliphatic groups for elastase).

The efficacy of the compounds for the treatment of various diseases can be determined by scientific methods which are known in the art. The following are noted as examples for HNE mediated conditions:

for acute respiratory distress syndrome, the method according to Human neutophil elastase (HNE) model (AARD 141:227–677 (1990), or the Endotoxin induced acute lung injury model in minipigs (*AARD* 142:782–788 (1990)) may be used;

in ischemia/reperfusion, the method according to the canine model of reperfusion injury (*J.Clin.Invest.* 81:624–629 (1988)) may be used.

The invention also provides pharmaceutical compositions containing a compound of the formula herein and the process of synthesis which include the intermediates for the manufacturing of the invention.

The compounds of the present invention may be preferably formulated into suitable pharmaceutical preparations such as tablets, capsules or elixirs, for oral administration or in sterile solutions or suspensions for parenteral administration. They can be administered to patients (human and animals) in need of such treatment in a dosage range of 5 to 500 mg per patient generally given several times, thus giving a total daily dose of from 5 to 2000 mg per day. The dose will vary depending on severity of disease, weight of patient and other factors.

The compounds may be formulated into pharmaceutical compositions by compounding 10 to 500 mg of a compound or mixture thereof or of a physiologically acceptable salt with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as micro-crystaline cellulose; a disintegrating agent such as corn starch, pregelantinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required. Pharmaceutical compositions containing the compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent permeable adhesive, is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

EXAMPLES

The compounds of the present invention, salts thereof, and their intermediates can be prepared or manufactured as described herein or by various process known to be present in the chemical art. By way of an example, the final step in the process defined herein necessitates an oxidation of a 2° alcohol to the ketone in Formula I. As described here, this transformation from alcohol to ketone was utilized by way of the procedure of N-chlorosuccinimide (NCS) and dimethylsulfide followed by treatment with base. However, alternative methods are known to perform a similar conversion that include dimethylsulfoxide and oxalyl chloride followed by base and 1,1,1-triacetoxy-1,-dihydro-1,2-benziodoxol-3(1H)-one (Dess-Martin's Periodinane), to mention two. Other methods may also be appropriate as described in Oxidation in Organic Chemistry by Milos Hudlicky, ACS Monograph 186 (1990).

By way of further example, the $R_2$ group is introduced by the appropriate selection of the chiral amino alcohol, either commercially available or prepared by methods available to one skilled in the art by way of reduction of the natural or unnatural amino acid. The amino alcohol is selectively protected allowing for the alcohol to be converted to the corresponding aldehyde. By way of an alternative process, an amino protected aldehyde may be obtained by a reductive method of an amide made from the desired nitrogen protected amino acid and N,O-dimethylhydroxylamine as described by Winreb (*Tetrahedron Lett*. 22:3815 (1981). The aldehyde is subsequently allowed to react with acetone cyanohydrin to give the amino protected cyanohydrin (see FIG. I). The cyanohydrin may also be prepared by a standard method using sodium or potassium cyanide. Alternatively, trimethylsilylylcyanide may be used to effect the same conversion from aldehyde to cyanohydrin after acidic workup of the O-trimethylsilylylcyanohydrin intermediate. The next step is the protection of the cyanohydrin's alcohol followed by the conversion of the nitrile to the amide oxime through the use of hydroxylamine. This intermediate allows for the incorporation the $R_1$ group into the heterocycle through the reaction of the amide oxime amine with an activated $R_1$ carboxylic acid. The carboxylic acid may be activated by way of an acid chloride or floride, anhydride or an active ester with the requirements of the appropriate activation dictated by the $R_1$ group. The resulting N-acylated amide oxime can be either isolated or allowed to proceed in the cyclization when subjected to elevated temperatures. If the N-acylated amide oxime is isolated it can be characterized and subsequently cyclized in a separate step to the 1,2,4-oxadiazole (see FIG. II).

In an anticipated analogy, the 1,2,4-triazole is envisioned by the reaction of an N-substituted hydrazine with the nitrile described herein. After acylation at either available nitrogen, the resulting intermediate is allowed to form the 1,3,5-tri-substituted-1,2,4-triazole (Formula I, Y=substituted N and X=N) under conditions similar to that required for the 1,2,4-oxadiazole.

As described in FIG. III, the alcohol and amine are deprotected by methods available to one skilled in the art and the resulting amine is then subsequently coupled to the desired $R_3$ carboxylic acid. The final step, as mentioned herein, is the conversion of the 2° alcohol to the ketone. This oxidation can be performed by a number of methods with one such method being the use of the intermediate resulting from the reaction between NCS and dimethyl sulfide with the 2° alcohol followed by base. This process affords the ketone and preserves the stereochemistry of the neighboring $R_2$ group.

The following examples are given to illustrate the invention and are not intended to be inclusive in any manner:

i) temperatures are given in degrees Celsius (C.); room temperature ranged from 17° to 26°;

ii) chromatography was performed as described by Still (*J.Org.Chem.* 43:2923 (1978)) using ICN silica gel (60 Å), thin layer chromatography was performed using silica gel 60 F254 (25 mm) precoated plates from EM Science;

iii) NMR chemical shift data is reported in parts per million (ppm) relative to tertamethylsilane (TMS, 0.00 ppm) for $^1$H and deuterated chloroform (CDCl$_3$, 77.00 ppm) for $^{13}$C; the abbreviaitons used for the peak shape for the $^1$H data are as follows: s-singlet; d-doublet; t-triplet; q-quartet; m-multiplet; and br-broad;

iv) the course of reactions was monitored by TLC using UV and/or staining by aqueous KMnO$_4$ as detection methods, yields and reaction times are presented as illustrations but should not be considered optimal;

v) evaporation of solvents was performed using a rotary evaporator under reduced pressure ranging between 5 and 35 mm Hg; the bath temperatures were between 17 and 50° C.;

vi) chemical symbols have the standard meanings as familiar to someone skilled in the art, by way of example the following have been used: mmol (millimoles), mol (mole), mL (milliliters), L (liters), mg (milligram), g (grams), min (minutes), h (hours), TLC (thin layer chromatography), $R_f$ (ratio between the distance traveled by the compound compared to that of the solvent as related to TLC), RP-HPLC (reverse phase-high pressure liquid chromatography), RT (room temperature).

Example I
Methods of Synthesis
(Benzyloxycarbonyl)-L-Valyl-N-[1-[3-[5-(3-Trifluoromethylbenzyl)-1,2,4-oxadiazolyl]carbonyl]-2-(S)-Methylpropyl]-L-Prolinamide.

To a stirred mixture of 0.68 g (5.1 mmol) of N-chlorosuccinimide in 15 mL of dry toluene at 0° C. was added 0.53 mL (7.3 mmol) of dimethylsulfide (DMS) under a nitrogen atmosphere. A white precipitate formed after the addition of DMS. After 30 minutes, the resulting suspension was cooled to −25° C. using a carbon tetrachloride and dry ice bath. A solution of (benzyloxycarbonyl)-L-valyl-N-[1-[3-[5-(3-trifluoromethylbenzyl)-1,2,4-oxadiazolyl] hydroxymethyl]-2-(S)-methylpropyl]-L-prolinamide (0.84 g, 1.27 mmol) in 20 mL of dry toluene, was added dropwise. The resulting mixture was stirred for 3 h at −25° C. and 0.75 mL (5.4 mmol) of triethylamine was added. After 15 minutes, the cold bath was removed and the reaction monitored by TLC; silica gel; ethyl acetate:hexanes (4:1). After 1 h, the mixture was diluted with ethyl acetate and washed with NaHCO$_3$ (saturated), brine and dried with anhydrous magnesium sulfate. The resulting residue was purified by column chromatography; silica gel, ethyl acetate:hexanes, (1:1 to 7:3) to give a semisolid 91.7% pure. The material was further purified via RP-HPLC isocratic CH$_3$CN:H$_2$O (3:2), to give the title compound as a white solid after lyophilization; TLC: $R_f$=0.69, ethyl acetate:hexane (4:1).

$^1$H NMR (CDCl$_3$): δ [0.90 (d, J=6.7 Hz); 0.96 (d, J=6.7 Hz); 1.01 (d, J=6.7 Hz); 1.02 (d, J=6.7 Hz); 12H]; 1.80–2.20 (m, 4H); 2.25–2.50 (m, 2H), 3.54–3.70 (m, 1H), 3.70–3.83 (m, 1H); 4.30–4.40 (m, 1H), 4.38 (S, 2H); 4.63 (dd, J$_1$=2.7 Hz, J$_2$=7.1 Hz, 1H); 5.11 (ABq, J=12.3 Hz, 2H), 5.29 (dd, J$_1$=5.0 Hz, J$_2$=7.3 Hz, 1H), 5.60 d, J=9.1 Hz, 1H); 7.30–7.40 (m, 5H), 7.45–7.64 (m, 6H).

$^{13}$C NMR (CDCl$_3$) δ 17.24, 17.59, 19.46, 19,81, 25.12, 27.08, 30.26, 31.43, 32.69, 47.78, 57.49, 59.70, 61.53, 66.96, 123.73 (q, J=272 Hz), 124.93 (q, J=3.7 Hz), 125.85 (q, J=3.8 Hz), 128.01, 128.13, 128.51, 129.63, 131.48 (q, J=32.6 Hz), 132.44, 133.41, 136.27, 156.42, 164.87, 171.10, 172.29, 178.65, 189.89.

IR (Deposit) 3429.2, 3299.0, 2968.5, 1719.2, 1680.3, 1632.1 cm$^{-1}$.

|  | $C_{33}H_{38}N_5O_6F_3$ | | | |
| --- | --- | --- | --- | --- |
|  | % C | % H | % N | % F |
| Theory | 60.27 | 5.82 | 10.65 | 8.67 |
| Found | 60.04 | 6.03 | 10.60 | 8.08 |

The intermediate (Benzyloxycarbonyl)-L-Valyl-N-[1-[3-[5-(3-Trifluoromethylbenzyl)-1,2,4-oxadiazolyl] hydroxymethyl]-2-(S)-Methylpropyl]-L-Prolinamide was prepared as follows:

a. N-Benzyloxycarbonyl-L-Valinol.

To a stirred solution of valinol (13.96 g, 0.14 mol) and triethylamine (18.87 mL, 0.14 mol) in 250 mL of dry methylene chloride cooled to 0° C. under a nitrogen atmosphere was added 19.3 mL (0.14 mol) of benzyl chloroformate dropwise over 20 min. After warming to RT overnight, the mixture was diluted with methylene chloride (100 mL) and washed with 1 N HCl (2×), brine and dried with anhydrous magnesium sulfate. The resulting mixture was filtered and evaporated to give 30.70 g (95.6%) of N-benzyloxycarbonyl-valinol as a white solid: $R_f$=0.27 (silica gel; 1:1 hexane:ethyl acetate). Used without further purification.

b. N-Benzyloxycarbonyl-L-Valinal.

To a stirred solution of N-benzyloxycarbonyl-L-valinol (8.80 g, 0.037 mol) and triethylamine (30.00 g, 41.3 mL, 0.30 mol) in 100 mL dimethylsulfoxide under a nitrogen atmosphere was added a solution of sulfur trioxide pyridine complex (20.62 g, 0.130 mol) in dimethylsulfoxide (100 mL) dropwise via an addition funnel. An ice water bath was used to maintain the temperature of the reaction mixture below room temperature during the addition. After 30 min the cooling bath was removed and the reaction was allowed to warm to room temperature over 2 h. The brown solution was acidified with cold 2 N HCl to approximately pH 2 and extracted with ether (3×150 mL). The combined organic layers were washed with brine, dried (anhydrous magnesium sulfate) and evaporated to give 7.40 g of N-benzyloxycarbonyl-L-valinal (84.8%) as a yellow oil. The resulting material can be used without purification or further purified using column chromatography (silica gel, 9:1 hexanes:ethyl acetate).

$^1$H NMR (CDCl$_3$) δ 0.95 (d, J=7.0 Hz, 3H), 1.04 (d, J=7.0 Hz, 3H), 2.20–2.40 (m, 1H), 4.34 (dd, J$_1$=4.1, J$_2$=7.4 Hz, 1H), 5.12 (s, 2H), 5.37 (brs, 1H), 7.34 (s, 5H), 9.65 (s, 1H).

c. 3-(S)-[(Benzyloxycarbonyl)amino]-2-Hydroxy-4-Methylpentanenitrile.

To a solution containing N-benzyloxycarbonyl-L-valinal 22.2 g, 0.094 mol) in methylene chloride (500 mL) and triethylamine (5.81 g, 8.0 mL, 0.057 mol) was added acetone cyanohydrin (24.23 g, 26.0 mL, 0.2847 mol). The reaction was allowed to stir at room temperature overnight and then concentrated under reduced pressure. The residue was taken up into ether and washed with brine (3×). The solvent was removed under reduced pressure and purified by column chromatography (silica gel; 1:2 acetone:hexane) to give 21.38 g (86.6%) of 3-(S)-[(benzyloxycarbonyl)amino]-2-hydroxy-4-methylpentanenitrile as a pale yellow oil; TLC $R_f$=0.33 (silica gel; 1:2 acetone:hexane).

¹H NMR (CDCl₃) δ 0.92–1.05 (m, 6H), [1.80–2.0 (m), 2.10–2.30 (m), 1H], [3.45–3.55 (m), 3.70–3.80 (m), 1H], 4.65 (m, 1H), [5.14 (s), 5.15 (s), 2H], 5.35 (d, J=4.8 Hz, 1H), 7.36 (s, 5H).

d. 3-(S)-[(Benzyloxycarbonyl)amino]-2-Acetoxy-4-Methylpentanenitrile.

To a solution containing 3-[(benzyloxycarbonyl)amino]-2-hydroxy-4-methylpentanenitrile (32.0 g, 0.12 mol) and pyridine (59 mL) was added acetic anhydride (73.6 g, 68 mL, 0.72 mol) dropwise at RT. After 3 h the reaction was diluted with ethyl acetate and washed with water. The organic layer was separated, dried (anhydrous magnesium sulfate) and evaporated. The residue was purified by column chromatography (silica gel, 1:1 hexane:ethyl acetate) to give 33.08 g (94.0%) of 3-(S)-[(benzyloxycarbonyl)amino]-2-acetoxy-4-methylpentanenitrile as a viscous yellow oil; TLC $R_f$=0.70 (silica gel, 1:1 hexane:ethyl acetate).

¹H NMR (CDCl₃) δ 0.95–1.09 (m, 6H), 1.82–2.20 (m, 1H), [2.06 (s), 2.09 (s), 3H], 3.86–4.04 (m, 1H), [4.90 (d, J=8.5 Hz), 4.93 (d, J=9.7 Hz), 1H], [5.12 (s), 5.14 (s), 5.15 (s), 5.16 (s), 2H], [5.48 (d, J=4.9 Hz), 5.58 (d, J=4.0 Hz), 1H], 7.36 (s, 5H).

e. 1-[(N-Hydroxy)carboximidamido]-1-Acetoxy-2-(S)-Benzyloxycarbonyl amino-3-Methyl-Butane.

A solution containing 3-(S)-[(benzyloxycarbonyl)amino]-2-acetoxy-4-methylpentanenitrile (33.0 g, 0.11 mol), hydroxylamine hydrochloride (9.90 g, 0.14 mol) and sodium acetate (13.2 g, 0.16 mol) in a mixture of ethanol (330 mL) and water (66 mL) was heated to reflux under a nitrogen atmosphere for 3 h. The reaction mixture was concentrated, diluted with ethyl acetate and washed with water. The organic layer was dried (anhydrous magnesium sulfate), evaporated and purified via column chromatography to yield 22.5 g (58.2%) of 1-[(N-hydroxy)carboximidamido]-1-acetoxy-2-(S)-benzyloxycarbonyl amino-3-methyl-butane as a yellow foam. An analytical sample was prepared by RP-HPLC (C₁₈, 2:3 acetonitrile:water with 0.1% TFA, isocratic). The pure fractions were combined and evaporated. The residue was taken up into ethyl acetate, washed with dilute sodium bicarbonate, dried (anhydrous magnesium sulfate) and evaporated. The resulting residue was dissolved in dry ether, cooled to −78° C. under a nitrogen atmosphere and 1.1 equivalents of 4.0 N HCl in dioxane was added. The resulting white solid was collected by filtration and dried.

|  | $C_{16}H_{24}N_3O_5Cl$ | | |
|---|---|---|---|
|  | % C | % H | % N |
| Theory | 51.41 | 6.47 | 11.24 |
| Found | 51.30 | 6.40 | 11.17 | f. 3-Trifluoromethyl phenylacetyl Chloride.

To a mixture of 10.00 g (48.96 mmol) of 3-trifluoromethyl phenylacetic acid dissolved in 30 mL of dry methylene chloride was added 6.4 mL (9.33 g, 73.44 mmol) of oxalyl chloride over 2 minutes. Two drops of DMF was added (gas evolution) and the reaction was allowed to stir for 2 h at RT (gas evolution stopped). The reaction mixture was evaporated (40° C., aspirator vacuum) to give (3-trifluoromethyl) phenylacetyl chloride as a yellowish oil, 10.74 g (98.5%). The product was used without further purification.

IR (neat) 1796.8 cm⁻¹ C=O (acid chloride).

g. 1-[(N-Hydroxy)carboximid-N-(3-Trifluoromethylphenylacetyl)-amido]-1-Acetoxy-2-(S)-Benzyloxycarbonylamino-3-Methyl-Butane. To 1-[(N-hydroxy)carboximidamido]-1-acetoxy-2-(S)-benzyloxycarbonyl-amino-3-methyl-butane (6.74 g, 20 mmol) was added 40 mL of dry toluene and 25 mL of chloroform under a nitrogen atmosphere. The solution was cooled in a brine/ice bath and 4.2 mL (30 mmol) of triethylamine was added. After 5 minutes, 3-trifluoromethyl phenylacetyl chloride (4.67 g, 21.0 mmol), dissolved in 25 mL of chloroform, was added dropwise over 10 minutes. The reaction mixture was allowed to warm to room temperature overnight. The reaction was determined to be complete by TLC (silica gel; ethyl acetate:hexane, 1:1). Visualization was realized by aqueous KMnO₄ staining, the amide oxime develops at RT whereas the product requires heating. The mixture was evaporated under reduced pressure and the residue purified by column chromatography (silica gel; ethyl acetate:hexane, 50:50 to 70:30) to give 4.08 g (40%) of 1-[(N-hydroxy)carboximid-N-(3-trifluoromethylphenylacetyl)amido]-1-acetoxy-2-(S)-benzyloxycarbonyl-amino-3-methyl-butane as an off-white solid.

¹H NMR (CDCl₃) δ [0.90 (d, J=6.8 Hz); 0.95 (d, J=6.8 Hz); 0.98 (d, J=6.8 Hz); 1.02 (d, J=6.8 Hz); 6H]; 1.82–2.00 (m, 1H), [1.95 (s); 2.09 (s); 3H]; 3.80–3.98 (m, 1H); [3.80 (s), 3.85 (s), 2H], 4.80–5.20 (m, 5H), 5.41 (t, J=6.5 Hz, 1H); 7.30–7.40 (m, 5H); 7.40–7.60 (ml 4H).

h. 1-[3-[5-(3-Trifluoromethylbenzyl)]-1,2,4-oxadiazolyl]-1-Acetoxy-2-(S)-Benzyloxycarbonylamino-3-Methyl-Butane.

To 1-[(N-hydroxy)carboximid-N-(3-trifluoromethylphenylacetyl) amido]-1-acetoxy-2-(S)-benzyloxycarbonylamino-3-methyl-butane (4.08 g, 7.8 mmol), was added dry toluene (100 mL) under a nitrogen atmosphere and heated to reflux for 60 h. The mixture was cooled to room temperature and evaporated to give an oil. This resulting material was purified by column chromatography (silica gel; ethyl acetate:hexane, 50:50 to 60:40) to give 3.62 g (91.8%) of 1-[3-[5-(3-trifluoromethylbenzyl)]-1,2,4-oxadiazolyl]-1-acetoxy-2-(S)-benzyloxycarbonylamino-3-methyl-butane as an oil.

¹H NMR (CDCl₃) δ [0.93 (d, J=6.7 Hz); 1.00 (d, J=6.7 Hz); 1.04 (d, J=6.7 Hz); 6H]; [1.54–1.68 (m); 1.73–1.87 (m), 1H]; [2.05 (s); 2.14 (s); 3H]; 4.00–4.20 (m, 1H), [4.24 (s), 4.31 (s); 2H]; [4.99 (s), 5.09 (s), 2H]; [5.03 (d, J=10.5 Hz), 5.37 (d, J=10.5 Hz); 1H], [6.08 (d, J=1.8 Hz), 6.10 (d, J=4.4 Hz), 1H], 7.28–7.62 (m, 9H).

i. 1-[3-[5-(3-Trifluoromethylbenzyl)]-1,2,4-oxadiazolyl]-2-(S)-Benzyloxycarbonylamino-3-Methyl-Butan-1-ol.

To 1-[3-[5-(3-trifluoromethylbenzyl)]-1,2,4-oxadiazolyl]-1-acetoxy-2-(S)-benzyloxycarbonylamino-3-methyl-butane (3.62 g, 7.16 mmol), was added 70 mL of methanol and stirred until homogeneous (10 minutes). To this resulting solution was added potassium carbonate (1.19 g, 8.59 mmol) dissolved in 20 mL of water. The reaction was monitored by TLC (silica gel; ethyl acetate:hexane, 7:3). After 45 minutes, the reaction was diluted with ethyl acetate and washed with water (2×). The organics were dried with anhydrous magnesium sulfate, filtered and the solvent removed under reduced pressure. The residue was purified by column chromatography (silica gel; ethyl acetate:hexane, 50:50 to 60:40) to give 2.45 g (74.1%) of 1-[3-[5-(3-trifluoromethylbenzyl)]-1,2,4-oxadiazolyl]-2-(S)-benzyloxycarbonylamino-3-methyl-butan-1-ol.

¹H NMR (CDCl₃) δ [0.92 (d, J=6.7 Hz); 0.96 (d, J=6.7 Hz); 0.98 (d, J=6.7 Hz); 1.06 (d, J=6.7 Hz); 6H]; [1.61–1.75

(m); 1.91–2.05 (m); 1H]; [3.42 (d, J=7.8 Hz), 3.60 (d, J=6.4 Hz); 1H]; [3.75–3.85 (m), 3.94–4.04 (m), 1H]; [4.22 (s), 4.26 (s); 2H]; 4.95–5.10 (m, 3H); [5.24 (d, J=9.4 Hz), 5.27 (d, J=9.9 Hz), 1H]; 7.20–7.60 (m, 9H).

j. 1-[3-[5-(3-Trifluoromethylbenzyl)]-1,2,4-oxadiazolyl]-2-(S)-Amino-3-Methyl-Butan-1-ol Hydrochloride.

The amine, 1-[3-[5-(3-trifluoromethylbenzyl)]-1,2,4-oxadiazolyl]-2-(S)-benzyloxycarbonylamino-3-methyl-butan-1-ol, was dissolved into 20 mL trifluoroacetic acid at room temperature. Once dissolved, the mixture was cooled in an ice bath and thioanisole was added. The resulting mixture was allowed to warm to room temperature overnight and evaporated to give an oil. The oil was dissolved into 50 mL of dry ether (0° C.) and 1.5 equivalents of HCl in dioxane was added to give a solid. The suspension was allowed to settle and the ether decanted. An additional volume of ether was added (50 mL) and decanted to remove remaining thioanisole. The resulting solid slowly became an oil which was dried under vacuum ($\approx$1 mm Hg) for 5 h to give 0.96 g (49.4%) of 1-[3-[5-(3-trifluoromethylbenzyl)]-1,2,4-oxadiazolyl]-2-(S)-amino-3-methyl-butan-1-ol hydrochloride.

$^1$H NMR (CDCl$_3$) δ 0.98–1.50 (m, 6H); 1.86–2.06 (m, 1H); 3.58–3.80 (m, 1H); 4.20–4.40 (m, 2H), [5.25 (d, J=8.0 Hz), 5.37 (d, J=3.4 Hz), 1H], 6.60–7.20 (brs, 1H), 7.20–7.70 (m, 4H), 7.90–8.20 (brs, 3H).

k. (Benzyloxycarbonyl)-L-Valyl-N-[1-[(3-[5-(3-Trifluoromethylbenzyl)-1,2,4-oxadiazolyl]hydroxymethyl]-2-(S)-Methylpropyl]-L-Prolinamide.

A solution of Cbz-Val-Pro-OH (1.09 g, 2.83 mmol) in 30 mL of dry DMF was cooled in a brine/ice bath. To this stirred mixture was added HOBt (0.45 g, 3.34 mmol) followed by EDCI (0.52 g, 2.70 mmol). After stirring for 30 minutes, 1-[3-[5-(3-trifluoromethylbenzyl)]-1,2,4-oxadiazolyl]-2-(S)-amino-3-methyl-butan-1-ol hydrochloride (0.94 g, 2.57 mmol) in 20 mL of dry DMF was added dropwise followed by N-methyl morpholine (0.39 g, 3.85 mmol) and the reaction allowed to stir overnight at 0° C. The mixture was diluted with ethyl acetate (250 mL) and washed with saturated NaHCO$_3$ (2×), 5% KHSO$_4$, brine and the organics dried with anhydrous magnesium sulfate. The mixture was filtered and the solvent removed under reduced pressure. The residue was purified by column chromatography (silica gel, ethyl acetate:hexane 60:40 to 75:25) to give (benzyloxycarbonyl)-L-valyl-N-[1-[(3-[5-(3-trifluoromethylbenzyl)-1,2,4-oxadiazolyl]hydroxymethyl]-2-(S)-methylpropyl]-L-prolinamide as a white foamy solid; 0.88 g (51.9%).

$^1$H NMR (CDCl$_3$) δ 0.75–1.15 (m, 12H); 1.70–2.30 (m, 5.5H), 2.40–2.65 (m, 0.5H); 3.45–3.60 (m, 1H); 3.61–5.85 (m, 1H), 3.90–4.05 (m, 1H); 4.10–4.65 (m, 2H); (4.23 (s), 4.30 (s); 2H]; 4.75–5.15 (m, 3H); 5.30–5.85 (m, 1H); [6.91 (d, J=9.2 Hz), 7.08 (d, J=9.5 Hz), 1H]; 7.15–7.80 (m, 9H); [8.02 (d, J=8.6 Hz), 8.38 (d, J=8.6 Hz), 1H];

Example II
(Benzyloxycarbonyl)-L-Valyl-N-[1-[(3-[5-(2-Phenylethyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(2-phenylethyl)-1,2,4-oxadiazolyl]hydroxymethyl]-2-(S)-methylpropyl]-L-prolinamide for the alcohol; an analytical sample was obtained from RP-HPLC (isocratic, CH$_3$CN:H$_2$O:3:2) as a white solid; $^1$H NMR (CDCl$_3$) δ [0.89 (d, J=6.9 Hz); 0.96 (d, J=6.9 Hz); 1.02 (d, J=6.9 Hz); 12H]; 1.80–2.20 (m, 4H); 2.22–2.40 (m, 2H); 3.18–3.36 (m, 5H); 3.57–3.69 (m, 1H); 3.70–3.86 (m, 1H); 4.36 (dd, J$_1$=6.6 Hz; J$_2$=9.0 Hz; 1H); 4.63 (dd, J$_1$=2.9 Hz, J$_2$=8.2 Hz, 1H); 5.10 (ABq, J=12.4 Hz, 2H); 5.32 (dd, J$_1$=4.9 Hz, J$_2$=7.6 Hz, 1H); 5.66 (d, J=9.1 Hz, 1H); 7.18–7.40 (m, 10H); 7.45 (d, J=7.40 Hz, 1H)

$^{13}$C NMR (CDCl$_3$) δ 17.24, 17.59, 19.45, 19.76, 25.11, 27.23, 28.41, 30.41, 31.44, 32.39, 47.76, 57.52, 59.76, 61.49, 66.93, 126.82, 127.99, 128.09, 128.17, 128.48, 128.73, 136.32, 138.88, 156.44, 164.74, 171.09, 172.20, 180.62, 190.18

IR (Deposit) 3298.4, 2964.8, 1719.1, 1683.9, 1630.6, 1525.7, 1452.9, 1230.4 cm$^{-1}$.

| C$_{33}$H$_{41}$N$_5$O$_6$ | | | |
|---|---|---|---|
| | % C | % H | % N |
| Theory | 65.65 | 6.85 | 11.60 |
| Found | 65.50 | 6.68 | 11.61 |

The intermediate (benzyloxycarbonyl)-L-valyl-N-[1-[(3-[5-(2-phenylethyl)-1,2,4-oxadiazolyl]hydroxymethyl]-2-(S)-methylpropyl]-L-prolinamide was prepared as follows:

a. 3-Phenylpropionyl Chloride.

To a mixture of 3-phenyl propionic acid (15.00 g, 0.10 mol) in 50 mL of dry methylene chloride was added 10.9 mL (0.15 mol) of oxalyl chloride over 5 minutes. The mixture was allowed to stir at RT overnight. The mixture was evaporated (40° C., aspirator vacuum) to an oil which was distilled bp$_{0.9 \text{ mm Hg}}$ 74–75° C. to afford 15.14 g (89.9%) of product as a clear colorless liquid.

IR (Neat) 1790.4 cm$^{-1}$.

b. 1-[(N-Hydroxy)carboximid-N-(3-phenylpropionyl)amido]-1-Acetoxy-2-(S)-Benzyloxycarbonylamino-3-Methyl-Butane.

This compound was prepared following substantially the same procedure as described in Example I, except 3-phenylpropionyl chloride was used as the acid chloride; 49.1%, off-white solid.

$^1$H NMR (CDCl$_3$) δ [0.89 (d, J=6.8 Hz); 0.93 (d, J=6.8 Hz); 0.96 (d, J=6.8 Hz); 1.00 (d, J=6.8 Hz); 6H]; 1.82–1.96 (m, 1H); [1.91 (s), 2.06 (s), 3H]; 2.66–2.80 (m, 2H); 2.92–3.04 (m, 2H); 3.82–3.94 (m, 1H); 4.76–5.42 (m, 6H), 7.10–7.50 (m, 10H).

c. 1-[3-[5-(2-Phenethyl)]-1,2,4-oxadiazolyl]-1-Acetoxy-2-(S)-Benzyloxycarbonylamino-3-Methyl-Butane.

This compound was prepared by a cyclization procedure as described in Example I utilizing 1-[(N-hydroxy)carboximid-N-(3-phenylpropionyl)amido]-1-acetoxy-2-(S)-benzyloxycarbonylamino-3-methyl-butane; oil (yield 86.7%).

$^1$H (CDCl$_3$) δ [0.90 (d, J=6.8 Hz); 0.97 (d, J=6.8 Hz); 0.98 (d, J=6.8 Hz); 1.02 (d, J=6.8 Hz); 6H]; [1.28–1.44 (m); 1.68–1.84 (m); 1H]; [2.05 (s), 2.12 (s); 3H]; 3.04–3.28 (m, 4H); 3.98–4.10 (m, 1H); [5.04 (s), 5.13 (s); 2H]; 5.02–5.06 (m, 1H); 5.41 (d, J=10.1 Hz; 1H); [6.06 (d, J=3.5 Hz); 6.09 (d, J=7.8 Hz); 1H]; 7.12–7.46 (m, 10H].

d. 1-[3-[5-(2-phenethyl)]-1,2,4-oxadiazolyl]-2-(S)-Benzyloxycarbonylamino-3-Methyl-Butan-1-ol.

The compound was prepared using the hydrolysis conditions in Example I with 1-[3-[5-(2-phenethyl)]-1,2,4-oxadiazolyl]-1-acetoxy-2-(S)-benzyloxycarbonylamino-3-methyl-butane, oil (yield 76.7%).

$^1$H (CDCl$_3$) δ [0.91 (d, J=6.9 Hz); 0.96 (d, J=6.9 Hz); 0.99 (d, J=6.9 Hz); 1.08 (d, J=6.9 Hz); 6H]; [1.38–1.52 (m), 1.91–2.03 (m), 1H]; 3.02–3.26 (m, 5H); [3.76–3.86 (m), 3.88–4.00 (m) 1H]; 4.92–5.28 (m, 4H), 7.15–7.50 (m, 10H).

e. 1-[3-[5-(2-Phenethyl)]-1,2,4-oxadiazolyl]-2-(S)-Amino-3-Methyl-Butan-1-ol Hydrochloride.

This compound was prepared following substantially the same procedure as described in Example I utilizing 1-(3-[5-(2-phenethyl)]-1,2,4-oxadiazolyl]-2-(S)-benzyloxycarbonylamino-3-methyl-butan-1-ol; Heavy oil (yield 81.3%); $^1$H (CDCl$_3$) δ [1.03 (d, J=6.9 Hz); 1.05 (d, J=6.9 Hz); 1.09 (d, J=6.9 Hz); 6H]; [1.76–1.87 (m), 1.87–2.01 (m), 1H]; 3.02–3.30 (m, 5H); [3.62–3.73 (m), 3.73–3.83 (m), 1H]; [5.28 (d, J=9.0 Hz); 5.44 (d, J=3.5 Hz); 1H]; 6.74–7.06 (brs, 1H); 7.10–7.42 (m, 5H); 8.00–8.20 (2brs, 3H).

f. (Benzyloxycarbonyl)-L-Valyl-N-[1-[(3-[5-(2-Phenethyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(2-phenethyl)]-1,2,4-oxadiazolyl]-2-(s)-amino-3-methyl-butan-1-ol to give (benzyloxycarbonyl)-L-valyl-N-[1-[(3-[5-(2-phenylethyl)-1,2,4-oxadiazolyl]hydroxymethyl]-2-(S)-methylpropyl]-L-prolinamide as a white solid (yield 46.8%).

$^1$H (CDCl$_3$) δ 0.70–1.14 (m, 12H); 1.50–2.60 (m, 6H); 2.90–3.30 (m, 3H); 3.50–4.90 (m, 5H); 4.90–5.30 (m, 9H); 5.40–5.75 (m, 1H); 6.75–7.65 (m, 10H).

Example III (Benzyloxycarbonyl)-L-valyl-N-[1-[(3-[5-(2-Methoxybenzyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(2-methoxybenzyl)-1,2,4-oxadiazolyl]hydroxymethyl]-2-(S)-methylpropyl]-L-prolinamide for the alcohol; R$_f$=0.74 (silica gel 4:1, ethyl actetate:hexane). An analytical sample was obtained from RP-HPLC (isocratic, CH$_3$CN:H$_2$O: 3:2) as a white solid; TLC, R$_f$=0.74 ethylacetate:hexane (4:1).

$^1$H NMR (CDCl$_3$) δ [0.88 (d, J=7.0 Hz); 0.95 (d, J=7.0 Hz); 1.01 (d, J=7.0 Hz), 12H]; 1.80–2.20 (m, 4H); 2.20–2.45 (m, 2H); 3.55–3.80 (m, 1H); 3.70–3.80 (m, 1H); 3.80 (s, 3H), 4.35 (s, 2H), 4.35 (dd, J$_1$=6.8 Hz; J$_2$=9.1 Hz; 1H); 4.62 (dd, J$_1$=2.6 Hz, J$_2$=7.8 Hz, 1H); 5.10 (ABq, J=12.4 Hz, 2H); 5.33 (dd, J$_1$=5.0 Hz, J$_2$=7.6 Hz, 1H); 5.61 (d, J=9.2 Hz, 1H); 6.87–7.00 (m, 2H); 7.20–7.50 (m, 7H).

$^{13}$C NMR (CDCl$_3$) δ 17.12, 17.55, 19.47, 19.81, 25.12, 27.26, 27.82, 30.42, 31.41, 47.75, 55.41, 57.46, 59.77, 61.37, 66.93, 110.67, 120.74, 127.99, 128.10, 128.49, 129.40, 130.60, 136.27, 156.41, 157.22, 164.73, 171.03, 172.14, 180.17, 190.20.

IR (Deposit) 3305.5, 2965.4, 1716.6, 1682.7, 1633.5 cm$^{-1}$.

| $C_{33}H_{43}N_5O_7$ | | | |
|---|---|---|---|
| | % C | % H | % N |
| Theory | 63.96 | 6.67 | 11.30 |
| Found | 63.78 | 6.49 | 11.19 |

The intermediate (benzyloxycarbonyl)-L-valyl-N-[1-[(3-[5-(2-methoxybenzyl)-1,2,4-oxadiazolyl]hydroxymethyl]-2-(S)-methylpropyl]-L-prolinamide was prepared as follows:

a. 2-Methoxyphenylacetyl Chloride.

To a mixture of 2-methoxyphenylacetic acid (10.00 g, 0.060 mol) in 40 mL of dry methylene chloride was added 7.88 mL (0.090 mol) of oxalyl chloride over 5 minutes. The mixture was allowed to proceed overnight. The mixture was evaporated (40° C., aspirator vacuum) to an oil which was used without further purification; 10.89 g (98.0%) clear colorless liquid.

IR (Neat) 1803.5 cm$^{-1}$.

b. 1-[(N-Hydroxy)carboximid-N-(2-methoxybenzyl)amido]-1-Acetoxy-2-(S)-Benzyloxycarbonylamino-3-Methyl-Butane.

This compound was prepared following substantially the same procedure as described in Example I, but 2-methoxyphenylacetyl chloride using as the acid chloride; 32.1%, off-white solid.

$^1$H NMR (CDCl$_3$) δ [0.89 (d, J=7.0 Hz); 0.93 (d, J=7.0 Hz); 0.99 (d, J=7.0 Hz); 1.01 (d, J=7.0 Hz); 6H]; 1.82–2.20 (m, 1H); [1.91 (s), 2.06 (s), 3H]; [3.73 (s), 3.75 (s), 3.79 (s), 3.81 (s), 3H]; 3.80–3.98 (m, 1H); 4.84–5.46 (m, 6H), 6.82–6.88 (m, 2H); 7.90–7.40 (m, 9H).

c. 1-[3-[5-(2-methoxybenzyl)]-1,2,4-oxadiazolyl]-1-Acetoxy-2-(S)-Benzyloxycarbonylamino-3-Methyl-Butane.

This compound was prepared by a cyclization procedure as described in Example I utilizing 1-[(N-hydroxy)carboximid-N-(2-methoxybenzyl)amido]-1-acetoxy-2-(S)-benzyloxycarbonylamino-3-methyl-butane; oil (yield 86.7%).

$^1$H (CDCl$_3$) δ [0.92 (d, J=6.7 Hz); 0.97 (d, J=6.7 Hz); 0.99 (d, J=6.7 Hz); 1.02 (d, J=6.7 Hz); 6H]; [1.45–1.60 (m); 1.70–1.82 (m); 1H]; [2.02 (s), 2.11 (s), 3H]; [3.76 (s), 3.77 (s), 3H]; 4.00–4.18 (m, 1H); (4.18 (s), 4.23 (s), 2H]; 4.99–5.14 (m, 2.5H); 5.59 (d, J=10.0 Hz, 0.5H); [6.07 (d, J=3.5 Hz); 6.12 (d, J=4.7 Hz), 1H]; 6.84–6.98 (m, 2H); 7.16–7.40 (m, 7H).

d. 1-[3-[5-(2-methoxybenzyl)]-1,2,4-oxadiazolyl]-2-(S)-Benzyloxycarbonylamino-3-Methyl-Butan-1-ol.

This compound was prepared using the hydrolysis conditions in Example I but with the intermediate 1-[3-[5-(2-methoxybenzyl)]-1,2,4-oxadiazolyl]-1-acetoxy-2-(S)-benzyloxycarbonylamino-3-methyl-butane, oil (yield 76.7%).

$^1$H (CDCl$_3$) δ [0.92 (d, J=6.7 Hz); 0.95 (d, J=6.7 Hz); 0.97 (d, J=6.7 Hz); 1.05 (d, J=6.7 Hz); 6H]; [1.52–1.66 (m); 1.90–2.30 (m); 1H]; [3.12 (d, J=8.2 Hz), 3.43 (d, J=5.9 Hz), 1H]; [3.75 (s), 3.76 (s), 3H]; [3.76–3.86 (m), 3.90–4.00 (m), 1H]; [4.18 (s), 4.20 (s); 2H]; 4.96–5.05 (m), 5.09 (ABq, J=12.1 Hz, 2H); [5.19 (d, J=9.8 Hz); 5.40 (d, J=10.7 Hz); 1H]; 6.80–7.00 (m, 2H); 7.15–7.45 (m, 7H).

e. 1-[3-[5-(2-methoxybenzyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(2-methoxybenzyl)]-1,2,4-oxadiazolyl]-2-(S)-benzyloxycarbonylamino-3-methyl-butan-1-ol; Heavy oil (yield 81.3%).

$^1$H (CDCl$_3$) δ [0.97 (d, J=7.0 Hz); 1.00 (d, J=7.0 Hz); 1.04 (d, J=7.0 Hz); 6H]; 1.84 2.00 (m, 1H); 3.58–3.68 (m, 1H); [3.71 (s), 3.72 (s), 3H]; [4.16 (s), 4.20 (s), 2H]; [5.20 (d, J=8.0 Hz), 5.30 (d, J=3.4 Hz), 1H]; 6.80–6.92 (m, 2H); 7.10–7.45 (m, 2H); 7.90–8.20 (2brs, 3H).

f. (Benzyloxycarbonyl)-L-Valyl-N-[1-[(3-[5-(2-methoxybenzyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(2-methoxybenzyl)]-1,2,4-oxadiazolyl]-2-(S)-amino-3-methyl-butan-1-ol to give (benzyloxycarbonyl)-L-valyl-N-[1-[(3-[5-(2-phenylethyl)oxadiazolyl]hydroxymethyl]-2-(S)-methylpropyl]-L-prolinamide as a white solid (yield 46.8%).

¹H (CDCl₃) δ 0.80–1.60 (m, 12H); 1.60–2.20 (m, 6H); 3.50–4.70 (m, 12H); 4.95–5.25 (m, 3H); 6.80–7.00 (m, 2H), 7.10–7.50 (m, 7H).

Example IV
(Benzyloxycarbonyl)-L-Valyl-N-[1-[(3-[5-(Trifluoromethyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(trifluoromethyl)-1,2,4-oxadiazolyl]hydroxymethyl]-2-(S)-methylpropyl]-L-prolinamide for the alcohol; $R_f$=0.64 (silica gel 1:1, ethyl actetate:hexane). Purification was conducted using column chromatography (silica gel 1:1, ethyl actetate:hexane) to give a white solid (51.7% Yield).

¹H NMR (CDCl₃) δ 0.82–0.87 (2d overlapping, 6H); 0.90 (d, J=6.9 Hz, 3H); 0.96 (d, J=6.9 Hz, 3H); 1.60–2.10 (m, 5H); 2.25–2.45 (m, 1H); 3.45–3.60 (m, 1H); 3.65–3.80 (m, 1H); 4.00 (t, J=8.3 Hz, 1H), 4.43 (dd, $J_1$=4.8 Hz, $J_2$=8.3 Hz, 1H), 4.81 (t, J=6.0 Hz; 1H); 5.01 (ABq, J=13.1 Hz, 2H); 7.25–7.45 (bs, 6H); 8.62 (d, J=6.5 Hz, 1H).

¹³C NMR (CDCl₃) δ 17.51, 18.41, 18.88, 19.56, 24.45, 28.60, 29.01, 29.74, 47.03, 57.81, 58.61, 61.71, 65.37, 127.62, 127.75, 128.31, 137.06, 156.16, 164.32, 170.04, 172.17, 188.17.

IR (Deposit) 3431, 3296, 3024, 2970, 2878, 1717, 1684, 1630 cm⁻¹.

| | $C_{26}H_{32}N_5O_6F_3$ | | |
|---|---|---|---|
| | % C | % H | % N |
| Theory | 55.02 | 5.68 | 12.34 |
| Found | 54.76 | 5.55 | 12.18 |

The intermediate (benzyloxycarbonyl)-L-valyl-N-[1-[(3-[5-(trifluoromethyl)-1,2,4-oxadiazolyl]hydroxymethyl]-2-(S)-methylpropyl]-L-prolinamide was prepared as follows:

a. 1-[3-[5-(Trifluoromethyl)]-1,2,4-oxadiazolyl]-1-Acetoxy-2-(S)-Benzyloxycarbonylamino-3-Methyl-Butane.

A solution containing 10.0 g (29.64 mmol) of 1-[(N-hydroxy)carboximidamide]-1-acetoxy-2-(S)-benzyloxycarbonylamino-3-methyl-butane and 12.4 mL (87.79 mmol) of trifluoroacetic anhydride in 180 mL of anhydrous toluene was heated to 90° C. under a nitrogen atmosphere. The reaction was monitored by TLC (silica gel; ethyl acetate:hexane 1:1). After 20 min, the solvent was removed under reduced pressure and the residue purified by column chromatography (silica gel; ethyl acetate:hexane, 1:1) to afford 6.35 g (51.6%) of product as a viscous pale yellow oil.

¹H (CDCl₃) δ 0.95–1.10 (m, 6H); 1.70–1.90 (m; 1H); [2.09 (s), 2.16 (s), 3H]; [3.94–4.06 (m), 4.08–4.20 (m) 1H]; [5.01 (s), 5.08 (s); 2H]; 4.95–5.15 (m, 1H); [6.08 (d, J=6.2 Hz); 6.13 (d, J=2.7 Hz); 1H]; 7.20–7.50 (m, 5H).

b. 1-[3-[5-(Trifluoromethyl))-1,2,4-oxadiazolyl]-2-(S)-Benzyloxycarbonylamino-3-Methyl-Butan-1-ol.

This compound was prepared using hydrolysis conditions in Example I but with the intermediate 1-[3-[5-(trifluoromethyl)]-1,2,4-oxadiazolyl]-1-acetoxy-2-(S)-benzyloxycarbonylamino-3-methyl-butane, oil (yield 72.7%).

¹H (CDCl₃) δ [0.97 (d, J=6.9 Hz), 1.01 (d, J=6.9 Hz), 1.09 (d, J=6.9 Hz), 6H]; [3.63 (d, J=8.0 Hz), 3.73 (d, J=7.1 Hz, 1H]; [3.66–3.76 (m), 3.93–4.03 (m), 1H]; 4.95–5.24 (m, 3H), 7.26–7.45 (m, 5H).

c. 1-[3-[5-(Trifluoromethyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(trifluoromethyl]-1,2,4-oxadiazolyl]-2-(S)-benzyloxycarbonylamino-3-methyl-butan-1-ol; Heavy oil (yield 83.8%);

¹H (DMSO-d₆) δ 0.80–1.15 (m, 6H), 1.85–2.15 (m, 1H); 3.25–3.35 (m, 1H); 5.10–5.25 (brs, 1H); [8.10 (brs) 8.15 (brs), 3H].

d. (Benzyloxycarbonyl)-L-Valyl-N-[1-[(3-(5-(trifluoromethyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(trifluoromethyl)]-1,2,4-oxadiazolyl]-2-(S)-amino-3-methyl-butan-1-ol to give (benzyloxycarbonyl)-L-valyl-N-[1-[(3-[5-(trifluoromethyl)-1,2,4-oxadiazolyl]hydroxymethyl]-2-(S)-methylpropyl]-L-prolinamide as a white solid (yield 63.1%); $R_f$=0.54, 3:2 ethyl acetate:hexane.

¹H (CDCl₃) δ 0.80–1.20 (m, 6H); 1.80–2.60 (m, 6H); 3.50–4.70 (m, 6H); 4.90–5.30 (m, 3H); 5.40–5.75 (m, 1H); 6.85–7.20 (m, 1H), 7.25–7.40 (m, 5H).

Example V
(Benzyloxycarbonyl)-L-Valyl-N-[1-[(3-[5-(methyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(methyl)-1,2,4-oxadiazolyl]hydroxymethyl]-2-(S)-methylpropyl]-L-prolinamide for the alcohol; $R_f$=0.42 (silica gel, 5:95, methanol:methylene chloride). Purification was conducted by column chromatography on silica gel (5:95, methanol:methylene chloride) to give a white solid (57.2%).

¹H NMR (DMSO-d₆) δ [0.90 (d, J=6.9 Hz); 0.96 (d, J=6.9 Hz); 1.02 (d, J=6.9 Hz), 12H]; 1.80–2.25 (m, 4H); 2.25–2.45 (m, 2H); 2.68 (s, 3H); 3.55 (dd, $J_1$=5.6 Hz, $J_2$=15.8 Hz, 1H); 3.71 (dd, $J_1$=7.1 Hz, $J_2$=16.0 Hz, 1H); 4.01 (t, J=8.3 Hz, 1H); 4.47 (dd, $J_1$=4.3 Hz, $J_2$=7.9 Hz, 1H); 4.92 (t, J=6.1 Hz, 1H), 5.01 (ABq, J=12.6 Hz, 2H); 7.35 (s, 5H); 7.40 (d, J=7.0 Hz, 1H); 7.44 (d, J=8.0 Hz, 1H).

¹³C NMR (CDCl₃) δ 12.12, 17.14, 17.56, 19.26, 19.62, 24.95, 27.22, 30.26, 31.27, 47.62, 57.44, 59.52, 61.27, 66.72, 127.88, 127.94, 128.35, 136.21, 156.37, 164.74, 171.13, 171.99, 178.01, 190.07.

| | $C_{26}H_{35}N_5O_6.0.5\ H_2O$ | | |
|---|---|---|---|
| | % C | % H | % N |
| Theory | 59.76 | 6.94 | 13.40 |
| Found | 59.98 | 6.69 | 13.16 |

The intermediate (benzyloxycarbonyl)-L-valyl-N-[1-[(3-[5-(methyl)-1,2,4-oxadiazolyl]hydroxymethyl]-2-(S)-methylpropyl]-L-prolinamide was prepared as follows:

a. 1-[3-(5-(Methyl)]-1,2,4-oxadiazolyl]-1-Acetoxy-2-(S)-Benzyloxycarbonylamino-3-Methyl-Butane.

This compound was prepared using a similar cyclization procedure as reported in Example IV except acetic anhydride was used, oil (66.9% yield).

¹H (CDCl₃) δ 0.94 (d, J=6.7 Hz), 0.99 (d, J=6.7 Hz), 1.00 (d, J=6.7 Hz) 1.03 (d, J=6.7 Hz), 6H); [1.44–1.66 (m), 1.72–1.86 (m), 1H]; [2.11 (s), 2.12 (s), 3H]; [2.53 (s), 2.60 (s), 3H]; 3.95–4.15 (m, 1H), 5.04 (ABq, J=12.2 Hz, 2H), 5.04–5.14 (m, 1H); [6.05 (d, J=3.4 Hz); 6.11 (d, J=4.9 Hz), 1H]; 7.28–7.40 (m, 5H).

b. 1-[3-[5-(Methyl)]-1,2,4-oxadiazolyl]-2-(S)-Benzyloxycarbonylamino-3-Methyl-Butan-1-ol.

This compound was prepared using hydolysis conditions in Example I but with the intermediate 1-[3-[5-(methyl)]-1,2,4-oxadiazolyl]-1-acetoxy-2-(S)-benzyloxycarbonylamino-3-methyl-butane, oil (yield 93.2%).

$^1$H (CDCl$_3$) δ [0.94 (d, J=6.7 Hz), 0.98 (d, J=6.7 Hz), 0.99 (d, J=6.7 Hz), 1.07 (d, J=6.7 Hz), 6H); [1.54–1.66 (m), 1.92–2.06 (m), 1H); [2.54 (s), 2.58 (s), 3H]; [3.09 (d, J=8.2 Hz), 3.31 (d, J=5.8 Hz), 1H]; [3.72–3.86 (m), 3.90–4.01 (m), 1H]; 4.97–5.20 (m, 3.5H), 5.35 (brd, J=9.9 Hz, 0.5H); 7.25–7.45 (m, 5H).

c. 1-[3-[5-(Methyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(methyl)]-1,2,4-oxadiazolyl]-2-(S)-benzyloxycarbonylamino-3-methyl-butan-1-ol; Heavy oil (yield 87.3%);

$^1$H (DMSO-d$_6$) δ [0.89 (d, J=7.0 Hz); 0.95 (d, J=7.0 Hz); 0.98 (d, J=6.7 Hz); 6H]; 1.70–1.86 (m, 1H); 2.62 (s, 3H); 3.15–3.35 (m, 1H); 4.85–5.05 (m, 1H); 7.90–8.10 (brs, 3H).

d. (Benzyloxycarbonyl)-L-Valyl-N-[1-[(3-[5-(Methyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(methyl)]-1,2,4-oxadiazolyl]-2-(S)-amino-3-methyl-butan-1-ol to give (benzyloxycarbonyl)-L-valyl-N-[1-[(3-[5-(trifluoromethyl)oxadiazolyl]hydroxymethyl]-2-(S)-methylpropyl]-L-prolinamide as a white solid (yield 44.9%); R$_f$=0.74, 9:1 methylene chloride:methanol.

$^1$H (CDCl$_3$) δ 0.80–1.20 (m, 12H); 1.70–2.25 (m, 6H); [2.52 (s), 2.59 (s), 3H]; 3.50–3.85 (m, 2H); 3.90–4.45 (m, 3H); 4.45–4.65 (m, 1H); [4.69 (d, J=8.1 Hz), 4.87 (d, J=11.9 Hz), 1H]; 4.96–5.16 (m, 2H); [5.64 (d, J=9.0 Hz), 5.85(d, J=9.0 Hz), 1H]; [6.91 (d, J=9.2 Hz), 7.14 (d, J=9.3 Hz), 1H], 7.34 (brs, 5H).

Example VI (Benzyloxycarbonyl)-L-valyl-N-[1-[(3-[5-(Difluoromethyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(difluoromethyl)-1,2,4-oxadiazolyl]hydroxymethyl]-2-(S)-methylpropyl]-L-prolinamide for the alcohol; R$_f$=0.48 (silica gel, 3:2, ethyl acetate:hexane). Purification was conducted by column chromatography on silica gel (1:1, ethyl acetate:hexane) to give a white solid (yield 49.2%).

$^1$H NMR (CDCl$_3$) δ 0.93 (d, J=7.0 Hz, 3H); 0.96 (d, J=7.0 Hz, 3H); 1.01 (d, J=7.0 Hz, 3H), 1.03 (d, J=7.0 Hz), 1.80–2.20 (m, 4H); 2.25–2.45 (m, 2H); 3.55–3.65 (m, 1H); 3.65–3.85 (m, 1H), 4.35 (t, J=7.0 Hz, 1H); 4.64 (d, J=6.0 Hz, 1H); 5.01 (ABq, J=12.2 Hz, 2H); 5.21 (t, J=5.6 Hz, 1H), 5.52 (d, J=9.4 Hz, 1H), 6.88 (t, J=51.7 Hz, 1H), 7.36 (s, 5H), 7.62 (d, J=6.5 Hz, 1H).

$^{13}$C NMR (CDCl$_3$) δ 17.54, 17.63, 19.47, 19.77, 25.16, 26.81, 30.07, 31.46, 47.85, 57.54, 59.59, 61.96, 67.03, 105.31 (t, J=195 Hz), 128.04, 128.18, 128.54, 136.27, 156.42, 164.71, 171.17, 172.53, 188.78.

IR (Deposit) 3430, 3304, 3027, 2969, 2878, 1717, 1682, 1630 cm$^{-1}$.

| | C$_{26}$H$_{33}$N$_5$O$_6$ | | |
|---|---|---|---|
| | % C | % H | % N |
| Theory | 56.82 | 6.05 | 12.74 |
| Found | 56.81 | 5.97 | 12.62 |

The intermediate (benzyloxycarbonyl)-L-valyl-N-[1-[(3-[5-(difluoromethyl)-1,2,4-oxadiazolyl]hydroxymethyl]-2-(S)-methylpropyl]-L-prolinamide was prepared as follows:

a. 1-[3-[5-(Dimethyl)]-1,2,4-oxadiazolyl]-1-Acetoxy-2-(S)-Benzyloxycarbonylamino-3-Methyl-Butane.

This compound was prepared using a similar cyclization procedure as reported in Example IV except difluoroacetic anhydride was used, oil (36.0% yield).

$^1$H (CDCl$_3$) δ [0.94 (d, J=6.7 Hz), 0.99 (d, J=6.7 Hz), 1.01 (d, J=6.7 Hz), 6H), 1.04 (d, J=6.7 Hz), 6H]; 1.58–1.92 (m; 1H), [2.10 (s), 2.15 (s), 3H]; 3.90–4.20 (m, 1H); 4.95–5.25 (m, 3H), [5.94 (t, J=53.2 Hz, 5.97 (t, J=53.2 Hz), 1H], [6.12 (d, J=5.2 Hz, 6.25 (d, J=5.0 Hz), 1H); 7.30–7.45 (m, 5H).

b. 1-[3-[5-(Difluoromethyl)]-1,2,4-oxadiazolyl]-2-(S)-Benzyloxycarbonylamino-3-Methyl-Butan-1-ol.

This compound was prepared using hydolysis conditions in Example I but with the intermediate 1-[3-[5-(difluoromethyl)]-1,2,4-oxadiazolyl]-1-acetoxy-2-(S)-benzyloxycarbonylamino-3-methyl-butane, oil (yield 70.1%).

$^1$H (CDCl$_3$) δ [0.95 (d, J=6.7 Hz), 1.00 (d, J=6.7 Hz), 1.08 (d, J=6.7 Hz), 6H]; [1.62–1.86 (m), 1.98–2.14 (m), 1H]; [3.25 (d, J=6.6 Hz), 3.60 (d, J=6.7 Hz), 1H]; [3.97 (ddd, J$_1$=5.3 Hz, J$_2$=7.9 Hz, J$_3$=9.8 Hz), 4.31 (ddd, J$_1$=5.5 Hz, J$_2$=7.8 Hz, J$_3$=9.7 Hz), 1H]; [5.03 (s), 5.10 (s), 2H]; 4.98–5.22 (m, 2H); [5.94 (t, J=54.3 Hz), 6.72 (t, J=54.3 Hz), 1H]; 7.27–7.40 (m, 5H).

c. 1-[3-[5-(Difluoromethyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(difluoromethyl]-1,2,4-oxadiazolyl]-2-(S)-benzyloxycarbonylamino-3-methyl-butan-1-ol; heavy oil (yield 81.8%);

$^1$H (DMSO-d$_6$) δ [0.93 (d, J=7.0 Hz); 0.96 (d, J=7.0 Hz); 0.98 (d, J=7.0 Hz); 1.01 (d, J=7.0 Hz), 6H]; 1.80–2.00 (m, 1H); 3.20–3.35 (m, 1H); [5.08 (t, J=5.9 Hz), 5.15 (t, J=4.8 Hz), 1H]; [7.30 (t, J=53 Hz), 7.55 (t, J=53 Hz), 1H], 8.05 (brs, 3H).

d. (Benzyloxycarbonyl)-L-Valyl-N-[1-[(3-[5-(Difluoromethyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(difluoromethyl)-1,2,4-oxadiazolyl]-2-(S)-amino-3-methyl-butan-1-ol to give (benzyloxycarbonyl)-L-valyl-N-(1-[(3-[5-(difluoromethyl)-1,2,4-oxadiazolyl]hydroxymethyl]-2-(S)-methylpropyl]-L-prolinamide as a white solid (yield 47.1%); R$_f$=0.27, 65% ethyl acetate:hexane.

$^1$H (CDCl$_3$) δ 0.84–1.18 (m, 12H); [1.78–2.20 (m), 2.20–2.32 (m), 6H]; 3.50–3.65 (m, 1H); 3.66–3.92 (m, 1H); 4.11–4.71 (m, 4H); 5.00–5.15 (m, 2.5H); 5.17 (dd, J$_1$=7.4 Hz, J$_2$=7.8 Hz, 0.5H); [5.49 (bd, J=9.3 Hz), 5.64 (d, J=8.8 Hz), 1H]; (6.77 (t, J=52.1 Hz), 6.80 (t, J=52.1 Hz), 1H); [6.88 (d, J=8.7 Hz), 7.12 (d, J=8.5 Hz), 1H]; 7.30–7.45 (m, 5H).

Example VII (Benzyloxycarbonyl)-L-Valyl-N-[1-[(3-[5-(benzyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(benzyl)-1,2,4-oxadiazolyl]hydroxymethyl]-2-(S)-methylpropyl]-L-prolinamide for the alcohol; $R_f$=0.30 (silica gel 3:2, ethyl actetate:hexane). The material was purified by column chromatography on silica gel (3:2, ethyl acetate:hexane) to give a white solid, 59.7% yield.

$^1$H NMR (CDCl$_3$) δ [0.88 (d, J=6.8 Hz); 0.94 (d, J=6.8 Hz); 1.00 (d, J=6.8 Hz), 12H]; 1.80–2.20 (m, 4Hz; 2.20–2.45 (m, 2H); 3.55–3.70 (m, 1H); 3.75–3.85 (m, 1H); 4.30 (s, 2H), 4.30–4.40 (m, 1H); 4.61 (dd, J$_1$=2.4 Hz; J$_2$=7.7 Hz; 1H); 5.09 (ABq, J=12.0 Hz, 2H); 5.30 (dd, J$_1$=5.1 Hz, J$_2$=7.1 Hz, 1H); 5.60 (d, J=9.3 Hz, 1H); 7.25–7.50 (m, 11H).

$^{13}$C NMR (CDCl$_3$) δ 17.07, 17.59, 19.29, 19.69, 24.97, 27.26, 30.19, 31.27, 32.82, 47.64, 57.46, 59.56, 61.31, 66.75, 127.75, 127.90, 127.96, 128.37, 128.86, 128.91, 132.47, 136.24, 156.39, 164.71, 171.14, 172.02, 179.44, 189.97.

IR (Deposit) 3429, 3027, 3013, 2969, 1721, 1683, 1635, 1574, 1509, 1436 cm$^{-1}$.

| | $C_{32}H_{39}N_5O_6$·0.5 H$_2$O | | |
|---|---|---|---|
| | % C | % H | % N |
| Theory | 64.20 | 6.73 | 11.70 |
| Found | 64.00 | 6.77 | 11.62 |

The intermediate (benzyloxycarbonyl)-L-valyl-N-[1-[(3-[5-(benzyl)-1,2,4-oxadiazolyl]hydroxymethyl]-2-(S)-methylpropyl]-L-prolinamide was prepared as follows:

a. 1-[3-[5-(Benzyl)]-1,2,4-oxadiazolyl]-1-Acetoxy-2-(S)-Benzyloxycarbonylamino-3-Methyl-Butane.

This compound was prepared using a similar cyclization procedure as reported in Example IV except phenylacetic anhydride was used, the oil was used without further purification; TLC $R_f$=0.77, silica gel, 3:2 (ethyl acetate:hexane).

b. 1-[3-[5-(Benzyl)]-1,2,4-oxadiazolyl]-2-(s)-Benzyloxycarbonylamino-3-Methyl-Butan-1-ol.

This compound was prepared using the hydrolysis conditions in Example I but with the intermediate 1-[3-[5-(benzyl)]-1,2,4-oxadiazolyl]-1-acetoxy-2-(S)-benzyloxycarbonylamino-3-methyl-butane, oil (yield 47.0%); TLC $R_f$=0.47, silica gel, 1:1 (ethyl acetate:hexane).

$^1$H (CDCl$_3$) δ [0.92 (d, J=6.7 Hz), 0.98 (d, J=6.7 Hz), 1.06 (d, J=6.7 Hz), 6H]; [1.56–1.72 (m); 1.92–2.20 (m); 1H]; [3.00–3.08 (bd), 3.22–3.30 (m), 1H]; 3.74–3.86 (m, 0.5H); 3.90–4.00 (m, 0.5H); [4.18 (s), 4.21 (s); 2H]; 4.94–5.32 (m, 4H); 7.20–7.50 (m, 10H).

c. 1-[3-[5-(Benzyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(benzyl)]-1,2,4-oxadiazolyl]-2-(S)-benzyloxycarbonylamino-3-methyl-butan-1-ol; Heavy oil (yield 74.9%).

$^1$H (CDCl$_3$) δ [0.99 (d, J=7.0 Hz); 1.01 (d, J=7.0 Hz); 1.06 (d, J=7.0 Hz); 1.07 (d, J=7.0 Hz); 6H]; 1.80–2.10 (m, 1H); 3.60–3.80 (m, 1H); 4.10–4.28 (m, 2H); [5.24 (d, J=8.3 Hz), 5.35 (d, J=2.6 Hz), 1H]; 6.10–6.60 (bs, 1H); 7.10–7.45 (m, 5H); 8.17 (brs, 3H).

d. (Benzyloxycarbonyl)-L-Valyl-N-[1-[(3-[5-(Benzyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(benzyl)]-1,2,4-oxadiazolyl]-2-(S)-amino-3-methylbutan-1-ol to give (benzyloxycarbonyl)-L-valyl-N-[1-[(3-[5-(benzyl)-1,2,4-oxadiazolyl]hydroxymethyl]-2-(S)-methylpropyl]-L-prolinamide as a white solid (yield 74.7%); TLC $R_f$=0.10, silica gel, 3:2 (ethyl acetate:hexane).

$^1$H (CDCl$_3$) δ 0.70–1.20 (m, 12H); [1.65–2.20 (m), 2.45–2.60 (m), 6H)]; 3.42–3.60 (m, 1H); 3.62–3.75 (m, 1H); 3.85–4.02 (m, 1H); 4.10–4.65 (m, 4H); 4.71–5.15 (m, 3H); 5.30–5.65 (m, 1H); [5.79 (d, J=9.2 Hz), 6.85 (d, J=8.5 Hz), 1H); [7.03 (d, J=9.8 Hz), 7.70 (brd), 1H]; 7.20–7.45 (m, 10H).

Example VIII (Benzyloxycarbonyl)-L-Valyl-N-[1-[(3-[5-(3-methoxybenzyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(3-methoxybenzyl)-1,2,4-oxadiazolyl]hydroxymethyl]-2-(S)-methylpropyl]-L-prolinamide for the alcohol; $R_f$=0.60 (silica gel 4:1, ethyl actetate:hexane). An analytical sample was obtained from RP-HPLC (isocratic, CH$_3$CN:H$_2$O: 60:40) as a white solid.

$^1$H NMR (CDCl$_3$) δ [0.88 (d, J=6.9 Hz); 0.96 (d, J=6.9 Hz); 1.02 (d, J=6.9 Hz), 12H]; 1.85–2.20 (m, 4H); 2.20–2.40 (m, 2H); 3.55–3.70 (m, 1H); 3.70–3.85 (m, 1H); 3.80 (s, 3H), 4.28 (s, 2H), 4.35 (dd, J$_1$=6.9 Hz; J$_2$=8.8 Hz; 1H); 4.62 (dd, J$_1$=2.6 Hz, J$_2$=7.8 Hz, 1H); 5.10 (ABq, J=12.4 Hz, 2H); 5.31 (dd, J$_1$=4.9 Hz, J$_2$=7.5 Hz, 1H); 5.59 (d, J=9.0 Hz, 1H); 6.80–7.00 (m, 3H); 7.20–7.45 (m, 7H).

$^{13}$C NMR (CDCl$_3$) δ 17.14, 17.60, 19.46, 19.84, 25.12, 27.28, 30.36, 31.38, 32.99, 47.83, 55.28, 57.34, 59.85, 61.48, 66.99, 113.43, 114.66, 121.25, 128.00, 128.14, 128.51, 130.09, 133.88, 136.25, 156.45, 160.00, 164.76, 171.07, 172.35, 179.49, 189.99.

IR (Deposit) 3303.2, 2965.8, 1720.2, 1682.0, 1632.0 cm$^{-1}$.

| | $C_{33}H_{41}N_5O_7$·0.5 H$_2$O | | |
|---|---|---|---|
| | % C | % H | % N |
| Theory | 63.04 | 6.73 | 11.14 |
| Found | 63.05 | 6.89 | 11.06 |

The intermediate (benzyloxycarbonyl)-L-valyl-N-[1-[(3-[5-(3-methoxybenzyl)-1,2,4-oxadiazolyl]hydroxymethyl]-2-(S)-methylpropyl]-L-prolinamide was prepared as follows:

a. 3-Methoxyphenylacetyl Chloride.

This acid chloride was prepared in a similar manner as for the acid chloride in Example I and was used without further purification.

b. 1-[(N-Hydroxy)carboximid-N-(3-methoxybenzyl)amido]-1-Acetoxy-2-(S)-Benzyloxycarbonylamino-3-Methyl-Butane.

This compound was prepared following substantially the same procedure as described in Example I, but 3-methoxyphenylacetyl chloride using as the acid chloride; 65.3%, off-white solid.

$^1$H NMR (CDCl$_3$) δ [0.89 (d, J=6.9 Hz); 0.93 (d, J=6.9 Hz); 0.96 (d, J=6.9 Hz); 1.00 (d, J=6.9 Hz); 6H]; 1.80–2.15 (m, 1H); [1.91 (s), 2.06 (s), 3H]; 3.60–3.95 (m, 1H); [3.70 (s), 3.74 (s), 3.78 (s), 3.79 (s), 3H]; 4.70–5.30 (m, 7H), [5.38

(d, J=7.0 Hz), 5.41 (d, J=6.3 Hz), 1H]; 6.78–6.92 (m, 3H); 7.18–7.40 (m, 6H).

c. 1-[3-[5-(3-Methoxybenzyl)]-1,2,4-oxadiazolyl]-1-Acetoxy-2-(S)-Benzyloxycarbonylamino-3-Methyl-Butane.

This compound was prepared in a similar manner by a cyclization procedure described in Example I utilizing 1-[(N-hydroxy)carboximid-N-(3-methoxybenzyl)amido]-1-acetoxy-2-(S)-benzyloxycarbonylamino-3-methyl-butane; oil (yield 77.2%).

$^1$H (CDCl$_3$) δ [0.93 (d, J=6.8 Hz), 1.00 (d, J=6.8 Hz), 1.04 (d, J=6.8 Hz), 6H]; [1.52–1.64 (m); 1.72–1.85 (m); 1H]; [2.05 (s), 2.14 (s), 3H]; 3.80 (s, 3H); 4.00–4.15 (m, 1H); [4.17 (s), 4.22 (s), 2H]; 4.95–5.15 (m, 2H); 5.04 (d, J=11.2 Hz, 0.5H); 5.47 (d, J=10.7 Hz, 0.5H); [6.10 (d, J=5.5 Hz); 6.12 (d, J=7.3 Hz), 1H]; 6.80–6.93 (m, 3H); 7.22–7.41 (m, 6H).

d. 1-[3-[5-(3-Methoxybenzyl)]-1,2,4-oxadiazolyl]-2-(S)-Benzyloxycarbonylamino-3-Methyl-Butan-1-ol.

This compound was prepared using the hydrolysis conditions in Example I but with the intermediate 1-[3-[5-(3-methoxybenzyl)]-1,2,4-oxadiazolyl]-1-acetoxy-2-(S)-benzyloxycarbonylamino-3-methyl-butane, oil (yield 83.6%).

$^1$H (CDCl$_3$) δ [0.93 (d, J=6.7 Hz); 0.98 (d, J=6.7 Hz); 1.00 (d, J=6.7 Hz); 1.08 (d, J=6.7 Hz); 6H]; [1.59–1.72 (m); 1.92–2.06 (m); 1H]; [3.02 (d, J=8.1 Hz), 3.21 (d, J=5.7 Hz), 1H]; [3.79 (s), 3.80 (s), 3H]; [3.76–3.86 (m), 3.92–4.02 (m), 1H]; [4.17 (s), 4.20 (s); 2H]; 4.98–5.10 (m, 1.5H); [5.01 (ABq, J=12.5 Hz), 5.11 (ABq, J=12.1 Hz), 2H]; 5.28 (d, J=10.4 Hz, 0.5H); 6.80–6.91 (m, 3H); 7.22–7.40 (m, 6H).

e. 1-[3-[5(3-methoxybenzyl)]-1,2,4-oxadiazolyl-2-(S)-Amino-3-Methyl-Butan-1-ol Hydrochloride.

This compound was prepared following substantially the same procedure as described in Example I utilizing 1-[3-[5-(3-methoxybenzyl)]-1,2,4-oxadiazolyl]-2-(S)-benzyloxycarbonylamino-3-methyl-butan-1-ol; heavy oil (yield 90.7%).

$^1$H (CDCl$_3$) δ 0.80–1.12 (m, 6H); [1.84–1.96 (m); 1.96–2.10 (m), 1H]; 3.60–3.75 (m, 1H); [3.74 (s), 3.76 (s), 3H]; 4.05–4.30 (m, 2H); [5.26 (d, J=8.4 Hz), 5.35 (d, J=3.1 Hz), 1H]; 6.76–6.90 (m, 3H); 7.16–7.22 (m, 1H); 8.08–8.25 (2brs, 3H).

f. (Benzyloxycarbonyl)-L-Valyl-N-[1-[(3-[5-(3-methoxybenzyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(3-methoxybenzyl)]-1,2,4-oxadiazolyl]-2-(S)-amino-3-methyl-butan-1-ol to give (benzyloxycarbonyl)-L-valyl-N-[1-[(3-[5-(3-phenylethyl)-1,2,4-oxadiazolyl]hydroxymethyl]-2-(S)-methylpropyl]-L-prolinamide as a white solid (yield 50.8%).

$^1$H (CDCl$_3$) δ 0.76–1.12 (m, 12H); 1.65–2.25 (m, 6H); 3.45–3.80 (m, 2H); 3.77 (s, 3H); 3.85–4.05 (m, 0.5H); [4.10 (s), 4.18 (s), 2H]; 4.15–4.65 (m, 3H); 4.75–5.15 (m, 2.5H); [5.70 (d, J=9.1 Hz), 5.71 (d, J=8.9 Hz), 0.5H]; 6.11 (d, J=9.1 Hz, 0.5H]; 6.75–7.00 (m, 3.5H), 7.15–7.45 (m, 7.5H).

Example IX (Benzyloxycarbonyl)-L-Valyl-N-[1-[(3-[5-(2,6-difluorobenzyl)-1,2,4-oxadiazolyl]carbonyl)-2-(S)-Methylpropyl]-L-Prolinamide.

The compound was prepared using a similar oxidative procedure as described in Example I but utilizing (benzyloxycarbonyl)-L-valyl-N-[1-[(3-[5-(2,6-difluorobenzyl)-1,2,4-oxadiazolyl]hydroxymethyl]-2-(S)-methylpropyl]-L-prolinamide for the alcohol; R$_f$=0.24 (silica gel 1:1, ethyl actetate:hexane). The material was purified by column chromatography on silica gel (1:1, ethyl acetate:hexane) to give a white solid, 49.2% yield.

$^1$H NMR (CDCl$_3$) δ [0.87 (d, J=6.8 Hz); 0.94 (d, J=6.8 Hz); 1.02 (d, J=6.8 Hz), 12H]; 1.80–2.20 (m, 4H); 2.20–2.45 (m, 2H); 3.55–3.65 (m, 1H); 3.65–3.80 (m, 1H); 4.25–4.45 (m, 1H); 4.37 (s, 2H), 4.61 (dd, J$_1$=2.5 Hz; J$_2$=7.8 Hz; 1H); 5.09 (ABq, J=12.2 Hz, 2H); 5.28 (dd, J$_1$=4.9 Hz, J$_2$=7.3 Hz, 1H); 5.53 (d, J=9.3 Hz, 1H); 6.95 (t, J=8.5 Hz, 1H);7.29–7.40 (m, 8H).

$^{13}$C NMR (CDCl$_3$) δ 17.85, 17.56, 19.45, 19.79, 20.39, 25.11, 27.18, 30.31, 31.42, 47.74, 57.47, 59.71, 61.46, 66.92, 111.50 (dd, J$_1$=7.0 Hz, J$_2$=25.0 Hz), 128.00, 128.10, 128.48, 130.11 (t, J=10.3 Hz), 136.28, 156.41, 161.30 (dd, J$_1$=7.2 Hz, J$_2$=249.8 Hz), 164.86, 171.07, 172.16, 177.90, 189.90.

IR (Deposit) 3430, 3028, 1717, 1684, 1629, 1577, 1509, 1436 cm$^{-1}$.

| C$_{32}$H$_{37}$N$_5$O$_6$F$_2$.0.5 H$_2$O | | |
|---|---|---|
| | % C | % H | % N |
| Theory | 60.56 | 6.03 | 11.03 |
| Found | 60.53 | 6.15 | 10.90 |

The intermediate (benzyloxycarbonyl)-L-valyl-N-[1-[(3-[5-(2,6-difluorobenzyl)-1,2,4-oxadiazoyl ]hydroxymethyl-2-(S)-methylpropyl]-L-prolinamide was prepared as follows:

a. 1-[3-[5-(2,6-Difluorobenzyl)]-1,2,4-oxadiazolyl]-1-Acetoxy-2-(S)-Benzyloxycarbonylamino-3-Methyl-Butane.

This compound was prepared using a similar cyclization procedure as reported in Example IV except 2,6-difluorophenylacetic anhydride was used, yellow oil; TLC R$_f$=0.58, silica gel, 1:1 (ethyl acetate:hexane).

$^1$H (CDCl$_3$) δ 0.90–1.01 (m, 6H); 1.50–2.00 (m, 1H), [2.05 (s), 2.10 (s), 3H]; [3.76 (s), 3.86 (s), 2H]; 3.95–4.15 (m, 1H); 4.95–5.20 (m, 2.5H); 5.40–5.50 (brd, 0.5H); 6.00–6.15 (brs, 1H); 6.86–6.93 (m, 3H); 7.25–7.36 (m, 5H).

b. 1-[3-[5-(2,6-Difluorobenzyl)]-1,2,4-oxadiazolyl]-2-(S)-Benzyloxy carbonylamino-3-Methyl-Butan-1-ol.

This compound was prepared using the hydrolysis conditions in Example I but with the intermediate 1-[3-[5-(2,6-difluorobenzyl)]-1,2,4-oxadiazolyl]-1-acetoxy-2-(S)-benzyloxycarbonylamino-3-methyl-butane, oil (yield 49.8%); TLC R$_f$=0.47, silica gel, 1:1 (ethyl acetate:hexane).

$^1$H (CDCl$_3$) δ [0.92 (d, J=6.6 Hz), 0.95 (d, J=6.6 Hz), 0.96 (d, J=6.6 Hz), 1.04 (d, J=6.6 Hz), 6H]; 1.50–1.70 (m, 0.5H); 1.80–2.05 (m, 0.5H); [3.07 (d, J=8.1 Hz), 3.32 (d, J=6.2 Hz), 1H]; [3.70–3.82 (m), 3.90–3.98 (m), 1H]; [4.25 (s), 4.28 (s); 2H]; 4.98–5.15 (m, 3.5H); 5.27 (d, J=9.9 Hz, 0.5H); 6.89–6.95 (m, 2H); 7.20–7.38 (m, 6H).

c. 1-[3-[5-(2,6-Difluorobenzyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(2,6-difluorobenzyl)-]1,2,4-oxadiazolyl]-2-(S)-benzyloxycarbonylamino-3-methyl-butan-1-ol; Heavy oil (yield 90.5%).

$^1$H (DMSO-d$_6$) δ 0.90–1.02 (m, 6H); 1.70–1.95 (m, 1H); 3.10–3.35 (m, 1H); 4.38 (s, 2H); 4.80–4.95 (m, 0.5H); 5.00–5.10 (m, 0.5H); 7.00–7.50 (m, 3H); 8.01 (brs, 3H).

d. (Benzyloxycarbonyl)-L-Valyl-N-[1-[(3-[5-(2,6-Difluorobenzyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(2,6-difluorobenzyl)]-1,2,4-oxadiazolyl]-2-(S)-amino-3-methyl-butan-1-ol to give (benzyloxycarbonyl)-L-valyl-N-[1-[(3-[5-(2,6-difluorobenzyl)-1,2,4-oxadiazolyl]hydroxymethyl]-2-(S)-methylpropyl]-L-prolinamide as a white solid (yield 68.4%); TLC $R_f$=0.17, silica gel, 3:2 (ethyl acetate:hexane).

$^1$H (CDCl$_3$) δ 0.80–1.10 (m, 12H); [1.70–2.20 (m, 5.7H), 2.45–2.55 (m, 0.3H]; 3.50–3.65 (m, 1H); 3.66–3.80 (m, 1H); 3.85–3.94 (m, 1H); 4.05–4.66 (m, 4H); [4.80 (d, J=8.3 Hz), 4.88 (d, J=12.0 Hz), 1H]; 4.98–5.13 (m, 2H); [5.62 (d, J=9.3 Hz), 5.73 (d, J=9.2 Hz), 1H]; 6.03 (d, J=9.3 Hz, 0.5H); 6.83–6.97 (m, 1H); 7.17–7.35 (m, 8H); 7.72 (d, J=9.9 Hz, 0.5H).

Example X
(Benzyloxycarbonyl)-L-Valyl-N-[1-[(3-[5-(trans-styryl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-](3-[5-(trans-styryl)-1,2,4-oxadiazolyl]hydroxymethyl]-2-(S)-methylpropyl]-L-prolinamide; TLC $R_f$=0.25, (1:1, ethyl actetate:hexane). The material was purified by column chromatography on silica gel (1:1, ethyl acetate:hexane) to give a white solid.

$^1$H NMR (CDCl$_3$) δ [0.92 (d, J=6.9 Hz); 0.96 (d, J=6.9 Hz); 1.02 (d, J=6.9 Hz), 1.05 (d, J=6.9 Hz), 12H]; 1.80–2.25 (m, 4H); 2.25–2.45 (m, 2H); 3.55–3.70 (m, 1H); 3.76 (dd, J$_1$=6.0 Hz, J$_2$=8.3 Hz, 1H); 4.36 (dd, J$_1$=6.6 Hz, J$_2$=8.8 Hz, 1H); 4.65 (dd, J$_1$=2.5 Hz, J$_2$=8.0 Hz, 1H); 5.1 (ABq, J=12.3 Hz, 2H); 5.36 (dd, J$_1$=5.1 Hz, J$_2$=7.2 Hz, 1H); 5.55 (d, J=9.2 Hz, 1H); 7.04 (d, J=16.4 Hz, 1H); 7.30–7.70 (m, 11H); 7.98 (d, J=16.4 Hz, 1H).

$^3$C NMR (CDCl$_3$) δ 17.30, 17.57, 19.51, 19.85, 25.15, 27.19, 30.48, 31.46, 47.78, 57.48, 59.78, 61.53, 66.96, 109.11, 128.02, 128.15, 128.51, 129.14, 131.03, 133.97, 136.29, 143.00, 144.65, 156.43, 165.08, 171.04, 172.22, 176.73, 190.35.

IR (Deposit) 3429, 3028, 1717, 1682, 1641, 1580, 1509, 1437 cm$^{-1}$.

| $C_{33}H_{39}N_5O_6 \cdot H_2O$ | | | |
|---|---|---|---|
| | % C | % H | % N |
| Theory | 63.96 | 6.67 | 11.30 |
| Found | 64.40 | 6.41 | 11.29 |

The intermediate (benzyloxycarbonyl)-L-valyl-N-[1-[(3-[5-(trans-styryl)-1,2,4-oxadiazolyl]hydroxymethyl]-2-(S)-methylpropyl]-L-prolinamide was prepared as follows:

a. 1-[(N-Hydroxy)carboximid-N-(trans-Cinnamyl)amido]-1-Acetoxy-2-(S)-Benzyloxycarbonylamino-3-Methyl-Butane.

This compound was prepared following substantially the same procedure as described in Example I, except trans-cinnamyl chloride was used as the acid chloride; 48.1%; TLC $R_f$=0.42 and 0.31 (diastereomers), 3:2 ethyl acetate:hexane.

$^1$H (CDCl$_3$) d [0.93 (d, J=6.7 Hz), 0.98 (d, J=6.7 Hz), 1.00 (d, J=6.7 Hz), 1.04 (d, J=6.7 Hz), 6H]; [1.95 (s), 2.10 (s), 3H]; 1.90–2.02 (m, 1H); 3.90–4.04 (m, 1H); 4.89–5.31 (m, 5H); [5.47 (d, J=7.0 Hz), 5.48 (d, J=6.8 Hz), 1H]; [6.52 (d, J=16.0 Hz), 6.56 (d, J=16.0 Hz), 1H]; 7.28–7.55 (m, 10H); [7.79 (d, J=16.0 Hz), 7.80 (d, J=16.0 Hz), 1H].

b. 1-[3-[5-(trans-Styryl)]-1,2,4-oxadiazolyl)-1-Acetoxy-2-(S)-Benzyloxycarbonylamino-3-Methyl-Butane.

This compound was prepared using a similar cyclization procedure as reported in Example I except 1-[(N-hydroxy)carboximid-N-(trans-cinnamyl)amido]-1-acetoxy-2-(S)-benzyloxycarbonylamino-3-methyl-butane was used; viscous oil (yield 77.3%), TLC $R_f$=0.74 and 0.68 (diasteromers), silica gel, 3:2 (ethyl acetate:hexane).

$^1$H (CDCl$_3$) δ [0.96 (d, J=7.0 Hz), 1.01 (d, J=7.0 Hz), 1.03 (d, J=7.0 Hz), 1.05 (d, J=7.0 Hz), 6H]; [1.54–1.66 (m), 1.74–1.88 (m), 1H]; [2.06 (s), 2.14 (s), 3H]; 4.04–4.20 (m, 1H); 4.98–5.20 (m, 2.5H); 5.57 (d, J=10.5 Hz, 0.5 Hz); [6.11 (d, J=3.6 Hz), 6.16 (d, J=4.9 Hz), 1H]; [6.96 (d, J=16.4 Hz), 7.00 (d, J=16.4 Hz), 1H]; 7.28–7.61 (m, 10H); [7.80 (d, J=16.4 Hz), 7.84 (d, J=16.4 Hz), 1H].

c. 1-[3-[5-(trans-Styryl)]-1,2,4-oxadiazolyl]-2-(S)-Benzyloxycarbonylamino-3-Methyl-Butan-1-ol.

This compound was prepared using the hydrolysis conditions in Example I but with the intermediate 1-[3-[5-(trans-styryl)]-1,2,4-oxadiazolyl]-1-acetoxy-2-(S)-benzyloxycarbonylamino-3-methyl-butane, oil (yield 92.0%); TLC $R_f$=0.61, silica gel, 1:1 (ethyl acetate:hexane).

$^1$H (CDCl$_3$) δ [0.96 (d, J=6.7 Hz), 1.01 (d, J=6.7 Hz), 1.09 (d, J=6.7 Hz), 6H]; [1.60–1.80 (m), 1.95–2.15 (m), 1H]; [3.23 (d, J=8.1 Hz), 3.47 (d, J=6.0 Hz), 1H][3.80–3.95 (m), 3.95–4.10 (m), 1H]; 5.00–5.42 (m, 3.5H); 5.40 (d, J=10.3 Hz, 0.5 Hz); [6.95 (d, J=16.4 Hz), 6.98 (d, J=16.4 Hz), 1H]; 7.28–7.62 (m, 10H); [7.80 (d, J=16.4 Hz), 7.82 (d, J=16.4 Hz), 1H].

d. 1-[3-[5-(trans-Styryl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(trans-styryl)]-1,2,4-oxadiazolyl]-2-(S)-benzyloxycarbonylamino-3-methyl-butan-1-ol; yellow solid (yield 73.0%).

$^1$H (CDCl$_3$) δ [1.04 (d, J=6.7 Hz), 1.13 (d, J=6.7 Hz), 1.15 (d, J=6.7 Hz), 1.19 (d, J=6.7 Hz), 6H]; 1.85–2.20 (m, 1H); 3.55–3.70 (m, 1H); [5.26 (d, J=7.2 Hz), 5.41 (d, J=3.6 Hz), 1H]; 6.45 (brs, 1H); [7.00 (d, J=16.4 Hz), 7.03 (d, J=16.4 Hz), 1H]; 7.20–7.70 (m, 5H); [7.83 (d, J=16.4 Hz), 7.91 (d, J=16.4 Hz), 1H], 8.43 (bs, 3H).

e. (Benzyloxycarbonyl)-L-Valyl-N-[1-[(3-[5-(trans-Styryl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(trans-styryl)]-1,2,4-oxadiazolyl]-2-(S)-amino-3-methyl-butan-1-ol to give (benzyloxycarbonyl)-L-valyl-N-[1-[(3-[5-(trans-styryl)-1,2,4-oxadiazolyl]hydroxymethyl]-2-(S)-methylpropyl]-L-prolinamide as a white solid (yield 66.5%); TLC $R_f$=0.34 and 0.27 (diastereomers), silica gel, 7:3 (ethyl acetate:hexane).

$^1$H (CDCl$_3$) δ 0.87–1.10 (m, 12H); 1.65–2.65 (m, 6H); 3.50–3.85 (m, 2H); 3.90–4.95 (m, 4H); 5.00–5.20 (m, 2H); [5.39 (d, J=8.9 Hz), 5.42 (d, J=8.9 Hz), 5.60 (d, J=9.2 Hz), 5.82 (d, J=9.2 Hz), 1H]; 6.91–7.81 (m, 14H).

Example XI
(Benzyloxycarbonyl)-L-Valyl-N-[1-[(3-[5-(trans-4-Trifluoromethylstyryl)-1,2,4-oxadiazolyl]carbonyl)-2-(S)-Methylpropyl]-L-Prolinamide.

The compound was prepared using a similar oxidative procedure as described in Example I but utilizing (benzyloxycarbonyl)-L-valyl-N-[1-[(3-[5-(trans-4-trifluoromethylstyryl)-1,2,4-oxadiazolyl]hydroxymethyl]-2-(S)-methylpropyl]-L-prolinamide; TLC $R_f$=0.49, (3:2, ethyl actetate:hexane). The material was purified by column chromatography on silica gel (3:2, ethyl acetate:hexane) to give a white solid.

¹H NMR (CDCl₃) δ [0.93 (d, J=7.1 Hz); 0.96 (d, J=7.1 Hz); 1.02 (d, J=7.1 Hz), 1.05 (d, J=7.0 Hz), 12H]; 1.80–2.25 (m, 4H); 2.25–2.50 (m, 2H); 3.55–3.70 (m, 1H); 3.70–3.85 (m, 1H); 4.36 (dd, J₁=7.3 Hz, J₂=9.2 Hz, 1H); 4.66 (dd, J₁=2.2 Hz, J₂=7.7 Hz, 1H); 5.10 (ABq, J=12.5 Hz, 2H); 5.34 (dd, J₁=5.5 Hz, J₂=5.5 Hz, 1H); 5.52 (d, J=8.9 Hz, 1H); 7.13 (d, J=16.4 Hz, 1H); 7.30–7.45 (m, 4H); 7.48 (d, J=7.1 Hz, 1H); 7.71 (s, 5H); 7.98 (d, J=16.4 Hz, 1H).

¹³C NMR (CDCl₃) δ 17.35, 17.59, 19.49, 19.83, 25.15, 27.12, 30.42, 31.45, 47.79, 57.50, 59.73, 61.57, 66.96, 111.58, 126.10, 126.15, 128.02, 128.14, 128.27, 128.52, 132.63, 136.28, 137.20, 142.67, 156.43, 165.14, 171.10, 172.29, 176.08, 190.19.

IR (Deposit) 3430, 3026, 1719, 1681, 1641, 1510, 1509 cm⁻¹.

| $C_{34}H_{38}N_5O_6F_3$ | | | |
|---|---|---|---|
| | % C | % H | % N |
| Theory | 60.98 | 5.72 | 10.46 |
| Found | 60.88 | 5.74 | 10.50 |

The intermediate (benzyloxycarbonyl)-L-valyl-N-[1-[(3-[5-(trans-4-trifluoromethylstyryl)-1,2,4-oxadiazolyl] hydroxymethyl]-2-methylpropyl]-L-prolinamide was prepared as follows:

a. 1-[(N-Hydroxy)carboximid-N-(trans-4-trifluoromethylcinnamyl)amido]-1-Acetoxy-2-(S)-Benzyloxycarbonylamino-3-Methyl-Butane.

This compound was prepared following substantially the same procedure as described in Example I, except trans-4-trifluoromethylcinnamyl chloride was used as the acid chloride; 78.6%; TLC R_f=0.58 and 0.45 (diastereomers), 3:2 ethyl acetate:hexane.

¹H (CDCl₃) δ [0.92 (d, J=6.7 Hz), 0.97 (d, J=6.7 Hz), 0.99 (d, J=6.7 Hz), 1.03 (d, J=6.7 Hz), 6H]; [1.96 (s), 2.10 (s), 3H]; 1.80–2.10 (m, 1H); 3.85–4.10 (m, 1H); 4.95–5.30 (m, 5H); [5.46 (d, J=7.1 Hz), 5.47 (d, J=6.8 Hz), 1H]; [6.60 (d, J=16.0 Hz), 6.64 (d, J=16.0 Hz), 1H]; 7.24–7.42 (m, 4H); 7.55–7.70 (m, 5H); [7.78 (d, J=16.0 Hz), 7.79 (d, J=16.0 Hz), 1H].

b. 1-[3-[5-(trans-4-Trifluoromethylstyryl)]-1,2,4-oxadiazolyl]-1-Acetoxy-2-(S)-Benzyloxycarbonylamino-3-Methyl-Butane.

This compound was prepared using a similar cyclization procedure as reported in Example I except 1-[(N-hydroxy) carboximid-N-(trans-4-trifluoromethylcinnamyl)amido]-1-acetoxy-2-(S)-benzyloxycarbonylamino-3-methyl-butane was used; yellow solid (yield 72.6%), TLC R_f=0.90, silica gel, 1:1 (ethyl acetate:hexane).

¹H (CDCl₃) δ [0.96 (d, J=6.7 Hz), 1.01 (d, J=6.7 Hz), 1.05 (d, J=6.7 Hz), 6H]; [1.54–1.66 (m), 1.74–1.88 (m), 1H]; [2.07 (s), 2.15 (s), 3H]; 4.04–4.20 (m, 1H); [5.03 (s), 5.13 (s), 2H]; [5.07 (d, J=10.4 Hz), 5.48 (d, J=10.4 Hz), 1H]; [6.11 (d, J=3.5 Hz), 6.16 (d, J=5.1 Hz), 1H]; [7.02 (d, J=16.4 Hz), 7.07 (d, J=16.4 Hz), 1H]; 7.20–745 (m, 4H); 7.65–7.75 (m, 5H); [7.81 (d, J=16.4 Hz), 7.84 (d, J=16.4 Hz), 1H].

c. 1-[3-[5-(trans-4-Trifluoromethylstyryl)]-1,2,4-oxadiazolyl]-2-(S)-Benzyloxycarbonylamino-3-Methyl-Butan-1-ol.

This compound was prepared using the hydrolysis conditions in Example I but with the intermediate 1-[3-[5-(trans-4-trifluoromethylstyryl)]-1,2,4-oxadiazolyl]-1-acetoxy-2-(S)-benzyloxycarbonylamino-3-methyl-butane, yellow solid (yield 84.1%); TLC R_f=0.62, silica gel, 1:1 (ethyl acetate:hexane).

¹H (CDCl₃) δ [0.96 (d, J=6.6 Hz), 1.01 (d, J=6.6 Hz), 1.10 (d, J=6.6 Hz), 6H]; [1.60–1.80 (m), 1.95–2.15 (m), 1H]; [3.42 (d, J=8.0 Hz), 3.61 (d, J=6.0 Hz), 1H]; [3.80–3.95 (m), 3.95–4.10 (m), 1H]; 5.00–5.42 (m, 3H); [5.38 (d, J=10.3 Hz), 5.27 (d, J=9.5 Hz), 1H][7.03 (d, J=16.4 Hz), 7.06 (d, J=16.4 Hz), 1H]; 7.20–745 (m, 4H); 7.65–7.75 (m, 5H); [7.80 (d, J=16.4 Hz), 7.83 (d, J=16.4 Hz), 1H].

d. 1-[3-[5-(trans-4-Trifluoromethylstyryl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(trans-4-trifluoromethylstyryl)]-1,2,4-oxadiazolyl]-2-(S)-benzyloxycarbonylamino-3-methyl-butan-1-ol; white solid (yield 63.2%).

¹H (CDCl₃) δ [1.04 (d, J=6.6 Hz), 1.30–1.75 (m), 1.17 (d, J=6.6 Hz), 6H]; 1.85–2.20 (m, 1H); 3.55–3.70 (m, 1H); [5.26 (d, J=7.3 Hz), 5.44 (brd), 1H]; 6.60 (brs, 1H); [7.17 (d, J=16.4 Hz), 7.10 (d, J=16.4 Hz), 1H]; [7.28 (d, J=6.5 Hz), 7.37 (d, J=8.3), 1H]; 7.55–7.75 (m, 3H); [7.85 (d, J=16.4 Hz), 7.96 (d, J=16.4 Hz), 1H]; 8.43 (brs, 3H).

e. (Benzyloxycarbonyl)-L-Valyl-N-[1-[(3-[5-(trans-4-Trifluoromethylstyryl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(trans-4-trifluoromethylstyryl)]-1,2,4-oxadiazolyl]-2-(S)-amino-3-methyl-butan-1-ol to give (benzyloxycarbonyl)-L-valyl-N-[1-[(3-[5-(trans-styryl)-1,2, 4-oxadiazolyl]hydroxymethyl]-2-(S)-methylpropyl]-L-prolinamide as a yellow solid (yield 87.5%); TLC R_f=0.38 and 0.29 (diastereomers), silica gel, 7:3 (ethyl acetate:hexane).

¹H (CDCl₃) δ 0.84–1.14 (m, 12H); 1.65–2.65 (m, 6H); 3.50–3.85 (m, 2H); 3.902–4.90 (m, 4H); 5.00–5.20 (m, 2H); [5.56 (d, J=9.2 Hz), 5.88 (d, J=9.2 Hz), 1H]; [6.92–7.38 (m), 7.63–7.88 (m), 13H].

Example XII (Benzyloxycarbonyl)-L-Valyl-N-[1-[(3-[5-(trans-4-Methoxystyryl)-1,2,4-oxadiazolyl)carbonyl)-2-(S)-Methylpropyl]-L-Prolinamide.

The compound was prepared using a similar oxidative procedure as described in Example I but utilizing (benzyloxycarbonyl)-L-valyl-N-[1-[(3-[5-(trans-4-methoxystyryl)-1,2,4-oxadiazolyl]hydroxymethyl]-2-(S)-methylpropyl]-L-prolinamide; TLC R_f=0.38, (3:2, ethyl actetate:hexane). The material was purified by column chromatography on silica gel (3:2, ethyl acetate:hexane) to give a white solid.

¹H NMR (CDCl₃): δ 0.90 (d, J=6.8 Hz); 0.97 (d, J=6.8 Hz); 1.03 (d, J=6.8 Hz), 1.05 (d, J=6.8 Hz), 12H]; 1.90–2.48 (m, 6H); 3.60–3.70 (m, 1H); 3.74–3.84 (m, 1H); 3.74–3.84 (m, 1H); 3.87 (s, 3H); 4.35 (dd, J₁=7.0 Hz, J₂=9.2 Hz, 1H); 4.62 (dd, J₁=2.8 Hz, J₂=7.1 Hz, 1H).; 5.10 (ABq, J=12.2 Hz, 2H); 5.39 (dd, J₁=4.9 Hz, J₂=7.8 Hz, 1H); 5.67 (d, J=8.9 Hz, 1H); 6.90 (d, J=16.4 Hz, 1H); 6.96 (d, J=8.8 Hz, 1H); 7.25 (d, J=9.0 Hz, 1H); 7.35 (s, 5H); 7.56 (d, J=8.8 Hz, 2H); 7.93 (d, J=16.4 Hz, 1H).

¹³C NMR (CDCl₃) δ 17.10, 17.67, 19.42, 19.82, 25.12, 27.60, 30.63, 31.30, 47.94, 55.47, 57.66, 60.11, 61.49, 67.04, 106.44, 114.62, 126.72, 127.96, 128.15, 128.52, 129.97, 144.41, 156.53, 162.04, 164.90, 171.12, 172.53, 177.20, 190.36.

IR (Deposit) 3429, 3031, 2968, 1718, 1682, 1638, 1604, 1512 cm$^{-1}$.

| $C_{34}H_{41}N_5O_{67}.2\ H_2O$ | | |
|---|---|---|
| % C | % H | % N |
| Theory 61.16 | 6.79 | 10.49 |
| Found 61.59 | 6.38 | 10.02 |

The intermediate (benzyloxycarbonyl)-L-valyl-N-[1-[(3-[5-(trans-4-methoxystyryl)-1,2,4-oxadiazolyl]hydroxymethyl]-2-(S)-methylpropyl]-L-prolinamide was prepared as follows:

a. 1-[(N-Hydroxy)carboximid-N-(trans-4-methoxycinnamyl)amido]-1-Acetoxy-2-Benzyloxycarbonylamino-3-Methyl-Butane.

This compound was prepared following substantially the same procedure as described in Example I, except trans-4-methoxycinnamyl chloride was used as the acid chloride; 57.5%; TLC R$_f$=0.47 and 0.36 (diastereomers), 3:2 ethyl acetate:hexane.

$^1$H (CDCl$_3$) δ [0.92 (d, J=6.7 Hz), 0.97 (d, J=6.7 Hz), 0.99 (d, J=6.7 Hz), 1.04 (d, J=6.7 Hz), 6H]; [1.95 (s), 2.10 (s), 3H]; 1.88–2.25 (m, 1H); 3.84 (s, 3H); 3.90–4.10 (m, 1H); 4.90–5.33 (m, 5H); [5.47 (d, J=7.1 Hz), 5.49 (d, J=6.8 Hz), 1H]; [6.39 (d, J=15.9 Hz), 6.43 (d, J=15.9 Hz), 1H]; 6.91 (d, J=8.7 Hz, 2H); 7.25–7.40 (m, 4H); 7.49 (d, J=8.7 Hz, 1H); 7.50 (d, J=8.7 Hz, 1H); [7.44 (d, J=15.9 Hz), 7.75 (d, J=15.9 Hz), 1H].

b. 1-[3-[5-(trans-4-Methoxystyryl)]-1,2,4-oxadiazolyl]-1-Acetoxy-2-(S)-Benzyloxycarbonylamino-3-Methyl-Butane.

This compound was prepared using a similar cyclization procedure as reported in Example I except 1-[(N-hydroxy)carboximid-N-(trans-4-methoxycinnamyl)amido]-1-acetoxy-2-(S)-benzyloxycarbonylamino-3-methyl-butane was used; yellow solid (yield 53.4%), TLC R$_f$=0.74 and 0.68 (diastereomers), silica gel, 1:1 (ethyl acetate:hexane).

$^1$H (CDCl$_3$) δ [0.96 (d, J=6.6 Hz), 1.00 (d, J=6.6 Hz), 1.03 (d, J=6.6 Hz), 1.04 (d, J=6.6 Hz), 6H]; [1.50–1.68 (m), 1.74–1.90 (m), 1H]; [2.05 (s), 2.14 (s), 3H]; [3.85 (s), 3.86 (s), 3H]; 4.04–4.16 (m, 1H); [4.99–5.18 (m), 5.63 (d, J=10.6 Hz), 3H]; [6.11 (d, J=3.8 Hz), 6.16 (d, J=4.9 Hz), 1H]; [6.81 (d, J=16.3 Hz), 6.85 (d, J=16.3 Hz), 1H]; [6.94 (d, J=7.5 Hz, 2H); 6.95 (d, J=7.5 Hz, 2H]; 7.24–7.40 (m, 4H); 7.48–7.56 (m, 2H); [7.74 (d, J=16.4 Hz), 7.77 (d, J=16.4 Hz), 1H].

c. 1-[3-[5-(trans-4-Methoxystyryl)]-1,2,4-oxadiazolyl]-2-(S)-Benzyloxycarbonylamino-3-Methyl-Butan-1-ol.

This compound was prepared using the hydrolysis conditions in Example I but with the intermediate 1-[3-[5-(trans-4-methoxystyryl)]-1,2,4-oxadiazolyl]-1-acetoxy-2-(S)-benzyloxycarbonylamino-3-methyl-butane, (yield 85.2%); TLC R$_f$=0.61, silica gel, 3:2 (ethyl acetate:hexane).

$^1$H (CDCl$_3$) δ [0.95 (d, J=6.6 Hz), 1.00 (d, J=6.6 Hz), 1.09 (d, J=6.6 Hz), 6H]; [1.55–1.75 (m), 1.95–2.15 (m), 1H]; [3.21 (d, J=8.1 Hz), 3.47 (d, J=5.4 Hz), 1H]; 3.86 (s, 3H); 3.80–4.10 (m, 1H); 5.00–5.20 (m, 3H); [5.22 (d, J=9.8 Hz), 5.43 (d, J=10.0 Hz), 1H][6.80 (d, J=16.4 Hz), 6.83 (d, J=16.4 Hz), 1H]; 6.91–6.99 (m, 2H), [7.22–7.44 (m), 7.46–7.60 (m), 7H]; [7.74 (d, J=16.4 Hz), 7.76 (d, J=16.4 Hz), 1H].

d. 1-[3-[5-(trans-4-Methoxystyryl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(trans-4-methoxystyryl)]-1,2,4-oxadiazolyl]-2-(S)-benzyloxycarbonylamino-3-methyl-butan-1-ol; (yield 93.2%).

$^1$H (CDCl$_3$) δ [1.03 (d, J=6.9 Hz), 1.12 (d, J=6.9 Hz), 1.14 (d, J=6.6 Hz), 6H]; 1.88–2.12 (m, 1H); 3.56–3.68 (m, 1H); [3.83 (s), 3.84 (s), 3H]; [5.24 (d, J=7.1 Hz), 5.40 (d, J=3.7 Hz), 1H]; [6.83 (d, J=16.2 Hz), 6.87 (d, J=17.0 Hz), 1H]; [6.91 (d, J=6.8 Hz), 6.92 (d, J=7.0 Hz), 2H]; [7.51 (d, J=8.3 Hz), 7.53 (d, J=7.0 Hz), 2H]; [7.75 (d, J=16.3 Hz), 7.83 (d, J=16.4 Hz), 1H]; 8.42 (brs, 3H).

e. (Benzyloxycarbonyl)-L-Valyl-N-[1-[(3-[5-(trans-4-Methoxystyryl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(trans-4-methoxystyryl)]-1,2,4-oxadiazolyl]-2-(S)-amino-3-methyl-butan-1-ol to give (benzyloxycarbonyl)-L-valyl-N-[1-[(3-[5-(trans-methoxystyryl)-1,2,4-oxadiazolyl]hydroxymethyl]-2-methylpropyl]-L-prolinamide as a yellow solid (yield 87.5%); TLC R$_f$=0.25, silica gel, 7:3 (ethyl acetate:hexane).

$^1$H (CDCl$_3$) δ 0.84–1.14 (m, 12H); [1.60–2.22 (m), 2.48–2.60 (m), 6H]; 3.46–3.64 (m, 1H); 3.66 (m, 1H); [3.86 (s), 3.87 (s), 3H]; 3.92–4.90 (m, 4H); 5.02–5.18 (m, 2H); [5.36–5.64 (m), 5.95 (d, J=9.5 Hz), 1H]; [6.77 (d, J=16.4 Hz), 6.80 (d, J=16.4 Hz), 1H]; 6.88–7.10 (m, 2H), 7.12–7.60 (m, 9H); [7.72 (d, J=16.4 Hz), 7.73 (d, J=16.4 Hz), 1H].

Example XIII (Benzyloxycarbonyl)-L-valyl-N-[1-[(3-[5-(3-Thienylmethyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(3-thienylmethyl)-1,2,4-oxadiazolyl]hydroxymethyl]-2-(S)-methylpropyl]-L-prolinamide for the alcohol. The material was purified by column chromatography on silica gel (7:3, ethyl acetate:hexane); the material was further purified via RP-HPLC isocratic CH$_3$CN:H$_2$O (60:40), to give the title compound as a white solid after lyophilization; TLC: R$_f$=0.51, 7:3, ethyl acetate:hexane.

$^1$H NMR (CDCl$_3$) δ [0.88 (d, J=6.9 Hz); 0.95 (d, J=6.9 Hz); 1.01 (d, J=6.9 Hz), 1.02 (d, J=6.9 Hz), 12H]; 1.84–2.20 (m, 4H); 2.20–2.40 (m, 2H); 3.56–3.70 (m, 1H); 3.72–3.82 (m, 1H); 4.35 (s, 2H); 4.28–4.42 (m, 1H); 4.62 (dd, J$_1$=2.8 Hz; J$_2$=7.8 Hz; 1H); 5.10 (ABq, J=12.4 Hz, 2H); 5.31 (dd, J$_1$=4.8 Hz, J$_2$=7.3 Hz, 1H); 5.61 (d, J=8.9 Hz, 1H); 7.08 (d, J=5.0 Hz, 1H); 7.25 (s, 1H); 7.30–7.44 (m, 7H).

$^{13}$C NMR (CDCl$_3$) δ 17.12, 17.61, 19.39, 19.78, 25.07, 27.29, 27.67, 30.31, 31.34, 47.79, 57.53, 59.77, 61.44, 66.93, 123.71, 126.70, 127.85, 127.96, 128.09, 128.47, 131.78, 136.22, 156.44, 164.75, 171.13, 172.28, 179.08, 189.95.

IR (Deposit) 3429, 3026, 2968, 1718, 1683, 1635, 1577, 1437 cm$^{-1}$.

| $C_{32}H_{39}N_5O_6.1\ H_2O$ | | |
|---|---|---|
| % C | % H | % N |
| Theory 58.71 | 6.41 | 11.41 |
| Found 59.06 | 6.03 | 11.31 |

The intermediate (benzyloxycarbonyl)-L-valyl-N-[1-[(3-[5-(3-thienylmethyl)-1,2,4-oxadiazolyl]hydroxymethyl]-2-(S)-methylpropyl]-L-prolinamide was prepared as follows:

a. 1-[(N-Hydroxy)carboximid-N-(3-thienylacetyl)amido]-1-Acetoxy-2-(S)-Benzyloxycarbonylamino-3-Methyl-Butane.

This compound was prepared by a similar method as described in Example I but utilizing 3-thienylacetyl chloride as the acid chloride; pale yellow solid (yield 81.0%; TLC R$_f$=0. 49 and 0. 38 (diastereomers), silica gel, 3:2 (ethyl acetate:hexane).

$^1$H (CDCl$_3$) δ [0.89 (d, J=6.8 Hz), 0.94 (d, J=6.8 Hz), 0.97 (d, J=6.8) 1. 00 (d, J=6.8 Hz), 1.07 (d, J=6.8 Hz) 6H]; [1.80–2.00 (m), 2.04–2.18 (m), 1H]; [1.92 (s), 2.08 (s), 3H]; [3.76 (s), 3.80 (s), 2H]; 3.84–3.85 (m, 1H); 4.80–5.26 (m, 5H); 5.40 (t, J=7.0 Hz, 1H); [7.02–7.10 (m), 7.14–7.20 (m), 1H]; 7.28–7.40 (m, 8H).

b. 1-[3-[5-(3-Thienylmethyl)]-1,2,4-oxadiazolyl]-1-Acetoxy-2-(S)-Benzyloxycarbonylamino-3-Methyl-Butane.

This compound was prepared using a similar cyclization procedure as reported in Example I except 1-[(N-hydroxy)carboximid-N-(3-thienylacetyl)amido]-1-acetoxy-2-(S)-benzyloxycarbonylamino-3-methyl-butane was used, brown oil (yield 87.3%)TLC R$_f$=0.75, silica gel, 3:2 (ethyl acetate:hexane).

$^1$H (CDCl$_3$) δ [0.92 (d, J=6.7 Hz), 0.99 (d, J=6.7 Hz), 1.02 (d, J=6.7 Hz), 6H]; [1.52–1.70 (m), 1.72–1.81 (m), 1H]; [2.04 (s), 2.13 (s), 3H]; 4.00–4.18 (m, 1H); [4.21 (s), 4.26 (s), 2H]; [4.90–5.18 (m), 5.44 (d, J=10.4 Hz, 3H]; [6.08 (d, J=2.4 Hz, 6.10 (d, J=5.0 Hz, 1H]; [7.02–7.08 (m), 7.15–7.24 (m), 1H]; 7.26–7.40 (m, 7H).

c. 1-[3-[5-(3-Thienylmethyl)]-1,2,4-oxadiazolyl]-2-(S)-Benzyloxycarbonylamino-3-Methyl-Butan-1-ol.

This compound was prepared using the hydrolysis conditions in Example I but with the intermediate 1-[3-[5-(3-thienylmethyl)]-1,2,4-oxadiazolyl]-1-acetoxy-2-(S)-benzyloxycarbonylamino-3-methyl-butane, oil (yield 84.7%); TLC R$_f$=0.51, silica gel, 3:2 (ethyl acetate:hexane).

$^1$H (CDCl$_3$) δ [0.93 (d, J=6.7 Hz), 0.97 (d, J=6.7 Hz), 0.99 (d, J=6.7 Hz), 1.07 (d, J=6.7 Hz), 6H]; [1.62–1.80 (m); 1.90–2.04 (m); 1H]; [3.18 (d, J=8.1 Hz), 3.37 (d, J=6.1 Hz), 1H]; 3.74–3.84 (m), 3.90–4.02 (m), 1H]; [4.20 (s), 4.24 (s); 2H]; [4.94–5.19 (m), 5.27 (d, J=10.4 Hz), 4H] [7.03 (t, J=4.4 Hz), 7.15–7.22 (m), 1H]; 7.27–7.42 (m, 7H).

d. 1-[3-[5-(3-Thienylmethyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(3-thienylmethyl)]-1,2,4-oxadiazolyl]-2-(S)-benzyloxycarbonylamino-3-methyl-butan-1-ol; Heavy oil (yield 95.8%).

$^1$H (CDCl$_3$) δ [1.02 (d, J=6.7 Hz); 1.05 (d, J=6.7 Hz); 6H]; 1.84–2.02 (m, 1H); 3.60–3.80 (m, 1H); [4.22 (s), 4.27 (s), 2H]; [5.25 (d, J=8.0 Hz), 5.36 (d, J=3.6 Hz), 1H]; [7.00 (d, J=5.0 Hz), 7.03 (d, J=5.0 Hz), 1H]; 7.12–7.40 (m, 3H), 8.07 (brs, 3H).

e. (Benzyloxycarbonyl)-L-Valyl-N-[1-[(3-[5-(3-Thienylmethyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(3-thienylmethyl)]-1,2,4-oxadiazolyl]-2-(S)-amino-3-methyl-butan-1-ol to give (benzyloxycarbonyl)-L-valyl-N-[1-[(3-[5-(3-thienylmethyl)-1,2,4-oxadiazolyl]hydroxymethyl]-2-(S)-methylpropyl]-L-prolinamide as a solid (yield 54.5%); TLC R$_f$=0.06, silica gel, 7:3 (ethyl acetate:hexane).

$^1$H (CDCl$_3$) δ 0.80–1.15 (m, 12H); [1.70–2.20 (m), 2.44–2.56 (m), 6H]; 3.50–3.60 (m, 1H); 3.64–3.80 (m, 1H); 3.90–4.04 (m, 1H); 4.06–4.90 (m, 5H); 5.00–5.20 (m, 3H); [5.30–5.40 (m), 5.55–5.67 (m), 1H]; 6.02 (d, J=9.3 Hz, 0.5H), 6.84–7.08 (m, 2H); 7.15–7.40 (m, 7H); 7.68 (brd, 0.5H).

Example XIV
(Benzyloxycarbonyl)-L-Valyl-N-[1-[(3-[5-(4-Methoxybenzyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(4-methoxybenzyl)-1,2,4-oxadiazolyl]hydroxymethyl]-2-(S)-methylpropyl]-L-prolinamide for the alcohol. The material was purified initially by column chromatography (silica gel, 3:2 ethyl acetate:hexane), and further purified by RP-HPLC (isocratic, CH$_3$CN:H$_{22}$O: 60:40) to afford an analytical sample of the product as a white solid; R$_f$=0.36 (silica gel 3:2, ethyl acetate:hexane).

$^1$H NMR (CDCl$_3$) δ [0.88 (d, J=6.8 Hz); 0.95 (d, J=6.8 Hz); 1.01 (d, J=6.8 Hz), 12H]; 1.80–2.20 (m, 4H); 2.24–2.40 (m, 2H); 3.55–3.65 (m, 1H); 3.67–3.78 (m, 1H); 3.80 (s, 3H), 4.24 (s, 2H), 4.35 (dd, J$_1$=6.4 Hz; J$_2$ 9.1 Hz; 1H); 4.62 (dd, J$_1$=2.6 Hz, J$_2$=7.6 Hz, 1H); 5.10 (ABq, J=12.2 Hz, 2H); 5.30 (dd, J$_1$=5.2 Hz, J$_2$=7.5 Hz, 1H); 5.49 (d, J=9.2 Hz, 1H); 6.88 (d J=8.7 Hz, 2H); 7.26 (d, J=8.7 Hz, 2H); 7.36 (s, 5H); 7.38 (d, J=8.8 Hz, 1H).

$^{13}$C NMR (CDCl$_3$) δ 17.18, 17.54, 19.51, 19.86, 25.15, 27.12, 30.33, 31.44, 32.18, 47.77, 55.31, 57.46, 59.75, 61.46, 66.97, 111.44, 114.45, 124.51, 128.01, 128.14, 128.52, 130.12, 156.40, 158.91, 159.25, 171.00, 172.24, 179.90, 190.05.

IR (Deposit) 3432, 3036, 2969, 1717, 1687, 1633, 1620, 1514 cm$^{-1}$.

| C$_{33}$H$_{41}$N$_5$O$_7$ | | |
| --- | --- | --- |
| % C | % H | % N |
| Theory 63.96 | 6.67 | 11.30 |
| Found 63.71 | 6.79 | 11.59 |

The intermediate (benzyloxycarbonyl)-L-valyl-N-[1-[(3-[5-(4-methoxybenzyl)-1,2,4-oxadiazolyl]hydroxymethyl]-2-(S)-methylpropyl]-L-prolinamide was prepared as follows:

a. 4-Methoxyphenylacetyl Chloride.

This acid chloride was prepared in a similar manner as for the acid chloride in Example I and was used without further purification.

b. 1-[(N-Hydroxy)carboximid-N-(4-Methoxybenzyl)amido]-1-Acetoxy-2-(S)-Benzyloxycarbonylamino-3-Methyl-Butane.

This compound was prepared following substantially the same procedure as described in Example I, but 4-methoxyphenylacetyl chloride using as the acid chloride; 39.1%, off-white solid; TLC R$_f$=0.51 and 0.43 (diastereomers), silica gel 7:3 (ethyl acetate:hexane).

$^1$H NMR (CDCl$_3$) δ [0.89 (d, J=6.8 Hz); 0.93 (d, J=6.8 Hz); 0.99 (d, J=6.8 Hz); 1.06 (d, J=6.8 Hz); 6H]; [1.91 (s), 2.07 (s), 3H]; 1.80–2.20 (m, 1H); [3.66 (s), 3.70 (s), 2H]; [3.78 (s), 3.79 (s), 3H]; 3.80–3.95 (m, 1H); [4.80–5.24, 5.34–5.44 (m), 5H]; [6.83 (d, J=6.2 Hz), 6.86 (d, J=6.1 Hz); 2H]; [7.15–7.25 (m), 7.18–7.40 (m), 3H].

c. 1-[3-[5-(4-Methoxybenzyl)]-1,2,4-oxadiazolyl]-1-Acetoxy-2-(S)-Benzyloxycarbonylamino-3-Methyl-Butane.

This compound was prepared in a similar manner by a cyclization procedure described in Example I utilizing 1-[(N-hydroxy)carboximid-N-(4-methoxybenzyl)amido]-1-acetoxy-2-(S)-benzyloxycarbonylamino-3-methyl-butane; oil (yield 77.2%), TLC R$_f$=0.76, silica gel 3:2 (ethyl acetate:hexane).

$^1$H (CDCl$_3$) δ [0.92 (d, J=6.7 Hz), 0.98 (d, J=6.7 Hz), 1.01 (d, J=6.8 Hz), 6H]; [1.50–1.64 (m), 1.71–1.84 (m), 1H]; [2.03 (s), 2.18 (s), 3H]; [3.77 (s), 3.78 (s), 3H]; 3.96–4.22

(m, 3H); [4.84–5.18 (m), 5.47 (d, J=10.4 Hz), 3H]; [6.08 (d, J=5.3 Hz), 6.10 (d, J=7.0 Hz), 1H]; 6.80–6.92 (m, 2H); 7.16–7.42 (m, 7H).

d. 1-[3-[5-(4-Methoxybenzyl)]-1,2,4-oxadiazolyl]-2-(S)-Benzyloxycarbonylamino-3-Methyl-Butan-1-ol.

This compound was prepared using the hydrolysis conditions in Example I but with the intermediate 1-(3-(5-(4-methoxybenzyl)]-1,2,4-oxadiazolyl)-1-acetoxy-2-(S)-benzyloxycarbonylamino-3-methyl-butane, oil (yield 90.5%), TLC $R_f$=0.58, silica gel 3:2 (ethyl acetate:hexane).

$^1$H (CDCl$_3$) δ [0.92 (d, J=6.7 Hz); 0.96 (d, J=6.7 Hz); 0.98 (d, J=6.7 Hz); 1.06 (d, J=6.7 Hz); 6H]; [1.58–1.70 (m); 1.82–2.04 (m); 1H]; [3.09 (d, J=8.1 Hz), 3.29 (d, J=5.6 Hz), 1H]; [3.77 (s), 3.78 (s), 3H]; 3.90–4.02 (m, 1H); [4.12 (s), 4.15 (s); 2H]; [4.90–5.18 (m), 5.28 (d, J=10.0 Hz), 4H]; [6.84 (d, J=8.9 Hz), 6.86 (d, J=8.7 Hz), 2H]; [7.20 (d, J=8.5 Hz), 7.22 (d, J=8.7 Hz), 2H]; 7.28–7.39 (m, 5H).

e. 1-[3-[5-(4-Methoxybenzyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(4-methoxybenzyl)]-1,2,4-oxadiazolyl]-2-(S)-benzyloxycarbonylamino-3-methyl-butan-1-ol; heavy oil (yield 66.9%).

$^1$H (CDCl$_3$) δ 1.00 (d, J=6.7 Hz, 3H); 1.04 (d, J=6.7 Hz, 3H); 1.86–2.00 (m, 1H); 3.56–3.94 (m, 1H); [3.73 (s), 3.76 (s), 3H]; [4.10 (s), 4.16 (s), 2H]; [5.22 (d, J=7.8 Hz), 5.31 (d, J=3.3 Hz), 1H]; [6.81 (d, J=8.6 Hz), 6.82 (d, J=8.6), 2H]; [7.15 (d, J=8.6 Hz), 7.19 (d, J=8.6 Hz), 2H]; 8.03 (brd, 3H).

f. (Benzyloxycarbonyl)-L-Valyl-N-[1-[(3-[5-(4-Methoxybenzyl)- 1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(4-methoxybenzyl)]-1,2,4-oxadiazolyl]-2-(S)-amino-3-methyl-butan-1-ol to give (benzyloxycarbonyl)-L-valyl-N-[1-[(3-[5-(4-methoxybenzyl)-1,2,4-oxadiazolyl]hydroxymethyl]-2-(S)-methylpropyl]-L-prolinamide as a white solid (yield 50.8%); TLC $R_f$=0.35, silica gel 4:1 (ethyl acetate:hexane).

$^1$H (CDCl$_3$) δ 0.77–1.12 (m, 12H); [1.70–2.20 (m), 2.46–2.58 (m), 6H]; 3.46–3.74 (m, 2H); [3.76 (s), 3.78 (s), 3H]; 3.88–4.90 (m, 6H); 5.00–5.20 (m, 2H); [5.53 (d, J=9.3 Hz), 5.64 (d, J=9.4 Hz), 1H]; 5.93 (d, J=9.4 Hz, 0.5H); 6.76–6.90 (m, 2H); 7.08–7.44 (m, 8H); 7.72 (brd, 0.5H).

Example XV (Benzyloxycarbonyl)-L-Valyl-N-[1-[(3-[5-(Phenyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(phenyl)-1,2,4-oxadiazolyl]hydroxymethyl]-2-(S)-methylpropyl]-L-prolinamide for the alcohol. Purification was conducted using column chromatography (silica gel, 1:1 to 7:3, ethyl actetate:hexane) followed by purification by RP-HPLC, isocratic CH$_3$CN:H$_2$O (60:40), to give an analytical sample as a white solid after lyophilization; TLC: $R_f$=0.42, ethyl acetate:hexane (7:3).

$^1$H NMR (CDCl$_3$) δ [0.95 (d, J=6.8 Hz), 0.99 (d, J=6.8 Hz), 1.05 (d, J=6.8 Hz), 1.08 (d, J=6.8 Hz); 12H]; 1.80–2.25 (m, 4H); 2.25–2.50 (m, 2H); 3.55–3.70 (m, 1H); 3.70–3.85 (m, 1H); 4.30–4.45 (m, 1H), 4.60–4.75 (m, 1H); 5.12 (ABq, J=12.4 Hz, 2H); 5.37–5.44 (m, 1H), 5.57 (d, J=9.6 Hz, 1H); 7.25–7.70 (m, 10H), 8.62 (d, J=8.5 Hz, 1H).

$^{13}$C NMR (CDCl$_3$) δ 17.32, 17.59, 19.51, 19.86, 25.16, 27.23, 30.49, 31.46, 47.81, 57.51, 59.82, 61.61, 66.98, 123.26, 128.02, 128.14, 129.27, 133.53, 136.28, 156.44, 165.33, 171.09, 172.27, 177.17, 190.36.

| C$_{31}$H$_{37}$N$_5$O$_6$.0.5 H$_2$O | | | |
|---|---|---|---|
| | % C | % H | % N |
| Theory | 63.68 | 6.55 | 11.98 |
| Found | 63.51 | 6.45 | 11.71 |

The intermediate (benzyloxycarbonyl)-L-valyl-N-[1-[(3-[5-(phenyl)-1,2,4-oxadiazolyl]hydroxymethyl]-2-(S)-methylpropyl]-L-prolinamide was prepared as follows:

a. 1-[3-[5-(Phenyl)]-1,2,4-oxadiazolyl]-1-Acetoxy-2-(S)-Benzyloxycarbonylamino-3-Methyl-Butane.

This compound was prepared in a similar manner to that in Example IV except benzoic anhydride was used; yield (75.6%) of product as a viscous oil.

$^1$H (CDCl$_3$) δ [0.97 (d, J=6.7 Hz), 1.02 (d, J=6.7 Hz), 1.04 (d, J=6.7 Hz), 1.06 (d, J=6.7 Hz) 6H]; [1.56–1.70 (m), 1.76–1.90 (m), 1H]; [2.06 (s), 2.15 (s), 3H]; 4.10–4.21 (m, 1H); 4.96–5.20 (m, 2.5H); 5.61 (d, J=10.0 Hz, 0.5H); [6.16 (d, J=3.5 Hz), 6.21 (d, J=4.9 Hz), 1H]; 7.25–7.45 (m, 4H); 7.45–7.70 (m, 4H); 8.05–8.20 (m, 2H).

b. 1-[3-[5-(Phenyl)]-1,2,4-oxadiazolyl]-2-(S)-Benzyloxycarbonylamino-3-Methyl-Butan-1-ol.

This compound was prepared using hydolysis conditions in Example I but with the intermediate 1-[3-[5-(phenyl)]-1,2,4-oxadiazolyl]-1-acetoxy-2-(s)-benzyloxycarbonylamino-3-methyl-butane; oil (yield 53.3%), TLC: $R_f$=0.47 and 0.33 (diastereomers), ethyl acetate:hexane (1:1).

$^1$H (CDCl$_3$) δ [0.95 (d, J=7.0 Hz), 0.99 (d, J=7.0 Hz), 1.01 (d, J=7.0 Hz), 1.09 (d, J=7.0 Hz), 6H]; [1.71–1.85 (m), 1.94–2.09 (m), 1H]; 3.87–3.98 (m, 0.5H); 4.03–4.16 (m, 0.5H), 4.96–5.22 (m, 3.5H), 5.62 (d, J=9.3 Hz, 0.5H); 7.10–7.35 (m, 4H), 7.35–7.65 (m, 4H); 7.95–8.15 (m, 2H).

c. 1-[3-[5-(Phenyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(phenyl)]-1,2,4-oxadiazolyl]-2-(S)-benzyloxycarbonylamino-3-methyl-butan-1-ol; Heavy oil (yield 54.7%);

$^1$H (CDCl$_3$) δ 1.00–1.35 (m, 6H); 1.85–2.15 (m, 1H); 3.75–3.90 (m, 0.5H), 3.90–4.05 (m, 0.5H); [5.40 (d, J=8.9 Hz), 5.57 (d, T=2.6 Hz], 1H]; 7.30–7.60 (m, 3H); 7.95 (d, J=8.0 Hz, 1H); 8.09 (d, J=7.7 Hz, 1H); 8.17 (brs, 3H).

d. (Benzyloxycarbonyl)-L-Valyl-N-[1-[(3-[5-(Phenyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(phenyl)]-1,2,4-oxadiazolyl]-2-(S)-amino-3-methyl-butan-1-ol to give (benzyloxycarbonyl)-L-valyl-N-[1-[(3-[5-(phenyl)-1,2,4-oxadiazolyl]hydroxymethyl]-2-methylpropyl]-L-prolinamide as a white solid (yield 77.2%); $R_f$=0.41, 4:1 ethyl acetate:hexane.

$^1$H (CDCl$_3$) δ 0.80–1.20 (m, 12H); 1.65–2.65 (m, 6H); 3.45–3.85 (m, 2H); 3.90–4.05 (m, 0.5H); 4.05–4.65 (m, 3H); 4.70–5.20 (m, 3.5H); [5.21 (t, J=9.7 Hz), 5.38 (d, J=9.2 Hz), 1H]; 7.14 (d, J=9.5 Hz, 0.5H); 7.30–7.64 (m, 9.5H), [8.10 (d, J=8.0 Hz), 8.19 (d, J=8.0 Hz), 1H].

Example XVI (Benzyloxycarbonyl)-L-Valyl-N-[1-[(3-[5-(3-Phenylpropyl)-1,2,4-oxadiazolyl]carbonyl]-2-(S)-Methylpropyl]-L-Prolinamide.

The compound was prepared using a similar oxidative procedure as described in Example I but utilizing (benzyloxycarbonyl)-L-valyl-N-[1-[(3-[5-(3-phenylpropyl)-1,2,4-oxadiazolyl]hydroxymethyl]-2-(S)-methylpropyl]-L-prolinamide for the alcohol; an analytical sample was obtained from RP-HPLC (isocratic, $CH_3CN:H_2O$: 60:40) as a white solid; TLC $R_f$=0.29, 3:2 (ethyl acetate:hexane).

$^1H$ NMR ($CDCl_3$) δ [0.90 (d, J=6.9 Hz); 0.96 (d, J=6.9 Hz); 1.01 (d, J=6.9 Hz), 1.03 (d, J=6.9 Hz), 12H]; 1.82–2.40 (m, 6H); 2.20 (p, J=7.6 Hz, 2H); 2.74 (t, J=7.6 Hz, 2H); 2.96 (t, 7.6 Hz, 2H); 3.58–3.68 (m, 1H); 3.70–3.82 (m, 1H); 4.36 (dd, $J_1$=6.8 Hz; $J_2$=9.0 Hz; 1H); 4.60–4.63 (m, 1H); 5.10 (ABq, J=12.3 Hz, 2H); 5.34 (dd, J=4.9 Hz, $J_2$=9.0 Hz, 1H); 5.75 (d, J=9.1 Hz, 1H); 7.15–7.40 (m, 10H); 7.48 (d, J=7.4 Hz, 1H)

$^{13}C$ NMR ($CDCl_3$) δ 17.17, 17.59, 19.40, 19.77, 25.07, 27.78, 27.26, 27.76, 30.35, 31.39, 34.81, 47.73, 57.51, 59.71, 61.41, 66.88, 126.26, 127.96, 128.06, 128.41, 128.44, 128.50, 136.29, 140.23, 156.43, 164.71, 171.13, 172.14, 181.27, 190.17.

IR (Deposit) 3297.6, 2966.0, 1718.9, 1680.6, 1632.4 $cm^{-1}$.

|  | $C_{34}H_{47}N_5O_6$ | | |
| --- | --- | --- | --- |
|  | % C | % H | % N |
| Theory | 66.11 | 7.02 | 11.34 |
| Found | 65.87 | 7.25 | 11.27 |

The intermediate (benzyloxycarbonyl)-L-valyl-N-[1-[(3-[5-(3-phenylpropyl)-1,2,4-oxadiazolyl]hydroxymethyl]-2-(S)-methylpropyl]-L-prolinamide was prepared as follows:

a. 4-Phenylbutyryl Chloride.

The acid chloride was prepared in a similar manner as described in Example II except 4-phenylbutyric acid was used, the material was used without further purification.

b. 1-[(N-Hydroxy)carboximid-N-(4-phenylbutyryl)amido]-1-Acetoxy-2-(S)-Benzyloxycarbonylamino-3-Methyl-Butane.

This compound was prepared following substantially the same procedure as described in Example I, except 4-Phenylbutyryl chloride was used as the acid chloride; 34.1%, white solid, TLC $R_f$=0.41 and 0.33 (diastereomers), 1:1 (ethyl acetate:hexane).

$^1H$ NMR ($CDCl_3$) δ [0.91 (d, J=6.8 Hz); 0.95 (d, J=6.8 Hz); 0.98 (d, J=6.8 Hz); 1.02 (d, J=6.8 Hz); 6H]; [1.94 (s), 2.09 (s), 3H]; 1.84–2.12 (m, 3H); 2.36–2.47 (m, 2H); 2.64–2.73 (m, 2H); 3.84–3.96 (m, 1H); 4.76–5.24 (m, 5H); 5.30–5.45 (m, 1H); 7.14–7.40 (m, 10H).

c. 1-[3-[5-(3-Phenylpropyl)]-1,2,4-oxadiazolyl]-1-Acetoxy-2-(S)-Benzyloxycarbonylamino-3-Methyl-Butane.

This compound was prepared by a cyclization procedure as described in Example I utilizing 1-[(N-hydroxy)carboximid-N-(3-phenylpropionyl)amido]-1-acetoxy-2-(S)-benzyloxycarbonylamino-3-methyl-butane; oil (yield 85.7%), TLC $R_f$=0.63 and 0.60 (diastereomers), 1:1 (ethyl acetate:hexane).

$^1H$ NMR ($CDCl_3$) δ [0.94 (d, J=6.7 Hz); 0.99 (d, J=6.7 Hz); 1.00 (d, J=6.7 Hz); 1.03 (d, J=6.7 Hz); 6H]; [1.50–1.62 (m); 1.72–1.86 (m); 1H]; [2.05 (s), 2.13 (s); 3H]; 2.04–2.20 (m, 2H); 2.70 (q, J=7.7 Hz, 2H); [2.84 (t, J=7.7 Hz), 2.90 (t, J=7.7 Hz), 2H]; 4.00–4.13 (m, 1H); [5.00 (s), 5.11 (s); 2H]; [5.05 (d, J=10.4 Hz), 5.50 (d, J=10.6 Hz); 1H]; [6.08 (d, J=3.3 Hz); 6.11 (d, J=5.0 Hz); 1H]; 7.16–7.40 (m, 10H).

d. 1-[3-[5-(3-Phenylpropyl)]-1,2,4-oxadiazolyl]-2-(S)-Benzyloxycarbonylamino-3-Methyl-Butan-1-ol.

The compound was prepared using the hydrolysis conditions in Example I with 1-[3-[5-(3-phenylpropyl)]-1,2,4-oxadiazolyl]-1-Acetoxy-2-(S)-Benzyloxycarbonylamino-3-Methyl-Butane; oil (yield 76.7%), TLC $R_f$=0.44, 1:1 (ethyl acetate:hexane).

$^1H$ ($CDCl_3$) δ [0.94 (d, J=6.7 Hz); 0.98 (d, J=6.7Hz); 0.99 (d, J=6.7Hz); 1.08 (d, J=6.7 Hz); 6H]; [1.55–1.75 (m), 1.90–2.15 (m), 1H]; 2.13 (p, J=7.3 Hz, 2H); 2.69 (q, J=7.3 Hz, 2H); [2.84 (t, J=7.3 Hz), 2.87 (t, J=7.3 Hz), 2H]; [3.22 (d, J=8.0 Hz), 3.46 (d, J=6.0 Hz), 1H]; [3.76–3.86 (m), 3.92–4.02 (m), 1H]; 4.96–5.18 (m, 3H); [5.21 (d, J=9.5 Hz), 5.35 (d, J=10.0 Hz), 1H]; 7.14–7.40 (m, 10H).

e. 1-[3-[5-(3-Phenylpropyl)]-1,2,4-oxadiazolyl]-2-(S)-Amino-3-Methyl-Butan-1-ol Hydrochloride.

This compound was prepared following substantially the same procedure as described in Example I utilizing 1-[3-[5-(3-phenylpropyl)]-1,2,4-oxadiazolyl]-2-(S)-benzyloxycarbonylamino-3-methyl-butan-1-ol; heavy oil (yield 29.1%).

$^1H$ ($CDCl_3$) δ 1.10–1.80 (m, 6H); 1.80–2.05 (m, 1H); 2.00–2.20 (m, 2H); 2.68 (q, J=7.3 Hz, 2H); 2.77–2.92 (m, 2H); [5.26 (d, J=8.8 Hz), 5.42 (d, J=3.0 Hz), 1H]; 7.11–7.33 (m, 5H); 8.10–8.23 (m, 3H).

f. (Benzyloxycarbonyl)-L-Valyl-N-[1-[(3-[5-(3-Phenylpropyl)-1,2,4-oxadiazolyl]hydroxymethyl]-2-(S)-Methylpropyl]-L-Prolinamide.

This compound was prepared by a similar coupling procedure as described in Example I using the hydrochloride of 1-[3-[5-(3-phenylpropyl)]-1,2,4-oxadiazolyl]-2-(S)-amino-3-methyl-butan-1-ol to give (benzyloxycarbonyl)-L-valyl-N-[1-[(3-[5-(3-phenylpropyl)-1,2,4-oxadiazolyl]hydroxymethyl]-2-methylpropyl]-L-prolinamide as a white foamy solid (yield 60.3%).

$^1H$ ($CDCl_3$) δ 0.80–1.15 (m, 12H); 1.70–2.30 (m, 8H); 2.55–2.75 (m, 2H); 2.75–3.00 (m, 2H); 3.45–3.80 (m, 2H); 3.90–4.05 (m, 0.5H); 4.10–4.65 (m, 3H), 4.70–5.20 (m, 3.5H); [5.51 (t, J=8.1 Hz), 5.82 (d, J=9.4 Hz), 1H]; 6.92 (d, J=9.3 Hz, 0.5H); 7.06–7.40 (m, 10.5H).

Example XVII

Selectivity Studies

The $K_i$ values for different enzymes were determined as described above. The assay buffer was: 0.1 M HEPES, 0.1 M NaCl, 0.01 $CaCl_2$, 0.005% Triton X-100, 5% DMSO, pH 7.6. The chromogenic substrates were: Suc-[Ala-Ala-Pro-Leu]-pNA [(SEQ ID NO:1)]for α-chymotrypsin (bovine) and porcine pancreatic elastase, and Suc-[Ala-Ala-Pro-Phe]-pNA [(SEQ ID NO:2)]for human neutrophil cathepsin G.

| Enzyme | $K_i$ [μM] | Ratio |
| --- | --- | --- |
| HLE[a] | 0.0003 | 1 |
| PPE[b] | 0.0149 | 49.7 |
| α-CH[b] | 0.32 | 1068 |
| Cat-G[b] | >>30 | >1.0 × 10⁵ |

Buffers:
[a]0.05 M sodium phosphate, 0.1 M NaCl, 0.005% Tx-100, 5% DMSO, pH 7.5;
[b]0.1 M HEPES, 0.1 NaCl, 0.01 M $CaCl_2$, 0.005% Tx-100, 5.0% DMSO, pH 7.6.

Selectivity of Compound CE-2048: Porcine Pancreatic Elastase, Bovine α-Chymotrypsin and Human Cathepsin G (as compared to Human Leukocyte Elastase)

Example XVIII

Stability Studies (CE-2039, CE-2048 and CE-2049)

Stability of compounds in human plasma was determined as follows. Human plasma was obtained from two male and two female volunteers and previously stored frozen. Plasma was "spiked" with the compounds to a concentration of 0.025 nM. Samples were incubated 0, 3, and 6 hours at 37°. At each point protein was precipitated by addition of acetonitrile made 0.1 N HCl (3 parts of solution per part of sample). Samples were subjected to centrifugation (15–20 min at 14,000 rpm) and analyzed (200 μL) with reverse-phase HPLC using a 18–90% acetonitrile gradient in 0.1% TFA.

Example XIX $K_i$ Values

Enzyme was added to a mixture of nitroanilide substrate and inhibitor. The rate of aminolysis declined quickly to the steady-state level ($V_s$). Nitroaniline release from the substrate was monitored at 400–410 nm in an HP-5482 diode-array spectrophotometer. The $K_i^{app}$ values were calculated by a non-linear regression analysis program (ENZFITTER, Elsevier-Biosoft) using the following equations:

$$V_s = V_0/(1+[I]/K_i^{app})$$

$$K_i^{app} = K_i(1+[S]/k_m)$$

where [I] and [S] are the concentrations of inhibitor and substrate, respectively, $V_0$ and $V_s$ are the velocities of aminolysis in the absence and presence of inhibitor, respectively, $K_i^{app}$ and $K_i$ are apparent and true inhibition constants, respectively, and $K_m$ is the Michaelis constant. The inhibition assays were performed in 0.05 M sodium phosphate, 0.1 M NaCl, 0.005% Triton X-100, 5% DMSO, pH 7.6. The chromogenic substrates were: MeOSuc-[Lys(pic)-Ala-Pro-Val]-pNA [(SEQ ID NO:3)] and MeOSuc-[Ala-Ala-Pro-Val]-pNA [(SEQ ID NO:4)].

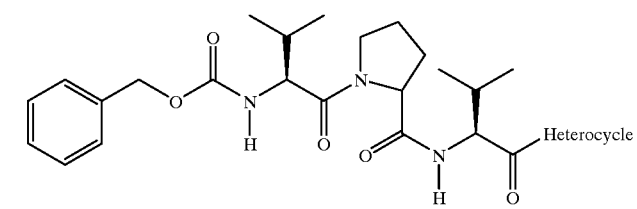

| $R_1$ | Heterocycle | $K_i$ (nM) |
|---|---|---|
| trifluoromethyl | (1,2,4-oxadiazole with CF$_3$) | 77 |
| methyl | (1,2,4-oxadiazole with CH$_3$) | 17 |
| difluoromethyl | (1,2,4-oxadiazole with CHF$_2$) | 7.2 |
| 2,6-difluorobenzyl | (1,2,4-oxadiazole with 2,6-difluorobenzyl) | 1.7 |
| benzyl | (1,2,4-oxadiazole with benzyl) | 2.0 |
| 2-thienylmethyl | (1,2,4-oxadiazole with 2-thienylmethyl) | 2.4 |

-continued
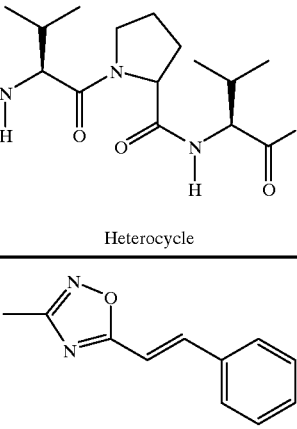
| $R_1$ | Heterocycle | $K_i$ (nM) |
|---|---|---|
| styryl | 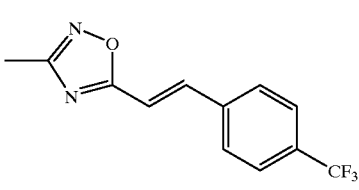 | 7.9 |
| 4-trifluoromethylstyryl | 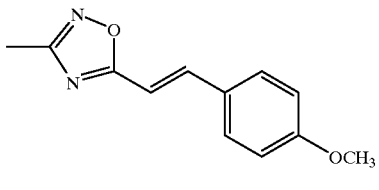 | 11.5 |
| 4-methoxystyryl | 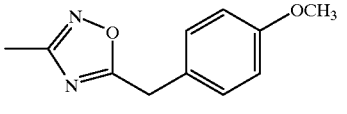 | 8.4 |
| 4-methoxybenzyl | 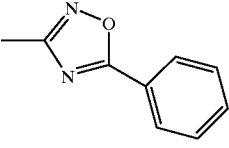 | 1.04 |
| phenyl | 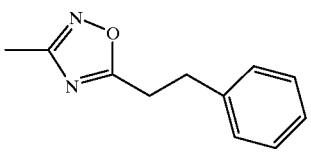 | 9.9 |
| 2-phenylethyl | 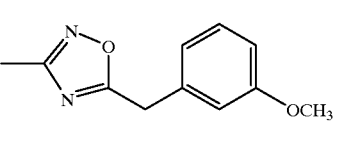 | 3.8 |
| 3-methoxybenzyl | 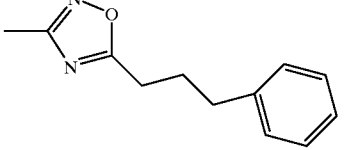 | 0.5 |
| 3-phenylpropyl | | 1.84 |

-continued

| $R_1$ | Heterocycle | $K_i$ (nM) |
|---|---|---|
| 3-trifluoromethylbenzyl | [3-methyl-1,2,4-oxadiazol-5-yl]methyl-(3-CF₃-phenyl) | 0.20 |
| 2-methoxybenzyl | [3-methyl-1,2,4-oxadiazol-5-yl]methyl-(2-OCH₃-phenyl) | 2.5 |
| 2-trifluoromethylphenyl choloromethyl | [3-methyl-1,2,4-oxadiazol-5-yl]-CHCl-(2-CF₃-phenyl) | 1.56 |

What is claimed is:

1. A compound of the formula wherein

X and Y are independently O, S or N wherein N is optionally substituted with alkyl, alkenyl, alkynyl being linear or branched; a phenyl, phenylalkenyl or phenylalkyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio groups being linear or branched; a heteroaryl, heteroarylalkyl or heteroarylalkenyl wherein the heteroaryl group is a monocyclic five or six membered ring containing one or two heteroatoms independently selected from oxygen, sulfur and nitrogen optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamide, arylcarboxamide, alkylthio or haloalkylthio groups being linear or branched, provided at least one of X or Y is N;

provided that where both X and Y are N, only one of X or Y is substituted;

$R_1$ is alkyl, alkenyl, haloalkenyl, alkynyl being linear or branched; a phenyl, phenylalkenyl or phenylalkyl optionally substituted with halogen, cyano, nitro, haloalkyl, amino, aminoalkyl, dialkylamino, alkyl, alkenyl, aLkynyl, alkoxy, haloalkoxy, carboxyl, carboalkoxy, alkylcarboxamide, arylcarboxamide, alkylthio or haloalkylthio being linear or branched; or a heteroaryl, heteroarylalkyl or heteroarylalkenyl wherein the heteroaryl group is a monocyclic five or six membered ring containing one or two heteroatoms independently selected from oxygen, sulfur and nitrogen optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxatnide, arylcarboxamide, alkylthio or haloalkylthio being linear or branched;

$R_2$ is a linear or branched alkyl, alkylthio, alkylthioalkyl, cycloalkyl, alkylcycloalkyl, phenyl or a phenylalkyl optionally substituted with halogen, cyano, nitro, hydroxyl, haloalkyl, alkylthio, terminal guanidine, guanidine, alkyl guanidine, dialkyl guanidine or amidine;

G is N or C optionally substituted with H, alkyl, cycloalkyl, aryl, heteroaryl or alkylheteroaryl;

$J_1$ and $J_2$ are independently selected from H, alkyl, cycloalkyl, aryl, heteroaryl, alkylaryl and alkylheteroaryl; and $J_3$ is H, alkylacyl, arylacyl, arylalkylacyl, alkyl-$SO_2$—, aryl-SO2—, alkylaryl-$SO_2$—, heterocycle-$SO_2$—, alkyl-NH—$SO_2$—, aryl-NH—$SO_2$—, alkylaryl-NH—$SO_2$ or heterocycle-NH—$SO_2$—;

or a pharmaceutically acceptable salt thereof.

2. The compound of claim 1 wherein $J_3$ is H, alkylacyl, arylacyl or arylalkylacyl.

3. The compound of claim 2 wherein $J_1$ is H, aryl or alkylaryl.

4. The compound of claim 3 wherein $J_2$ is H.

5. The compound of claim 4 wherein $R_2$ is aikyl.

6. The compound of claim 5 wherein $R_2$ is isopropyl.

7. The compound of claim 6 wherein X is O and Y is N, or X is N and Y is O.

8. The compound of claim 7 wherein $R_1$ is alkyl.

9. A method of inhibiting neutrophil elastase comprising administering to a host in need of such inhibition an effective amount of a compound of claim 1.

10. A method of treating acute respiratory disease comprising administering to a host in need of such treatment an effective amount of a compound of claim 1.

11. A method of treating myocardial ischemia-reperfusion injury comprising administering to a host in need of such treatment an effective amount of a compound of claim 1.

12. A pharmaceutical composition comprising a compound of claim 1 and a pharmaceutically acceptable carrier.

* * * * *

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic Tetrapeptide

<400> SEQUENCE: 1

Ala Ala Pro Leu
 1

<210> SEQ ID NO 2
<211> LENGTH: 4
<212> TYPE: PRT
<213> ORGANISM: Artificial Sequence
<220> FEATURE:
<223> OTHER INFORMATION: Synthetic Tetrapeptide

<400> SEQUENCE: 2

Ala Ala Pro Phe
 1

<210> SEQ ID NO 3
<211> LENGTH: 4
<212> TYPE: PRT
<213> ORGANISM: Artificial Sequence
<220> FEATURE:
<223> OTHER INFORMATION: Synthetic Tetrapeptide

```
<400> SEQUENCE: 3

Lys Ala Pro Val
 1

<210> SEQ ID NO 4
<211> LENGTH: 4
<212> TYPE: PRT
<213> ORGANISM: Artificial Sequence
<220> FEATURE:
<223> OTHER INFORMATION: Synthetic Tetrapeptide

<400> SEQUENCE: 4

Ala Ala Pro Val
```